United States Patent
Wu et al.

(10) Patent No.: US 11,950,904 B2
(45) Date of Patent: *Apr. 9, 2024

(54) NON-STEADY-STATE DETERMINATION OF ANALYTE CONCENTRATION FOR CONTINUOUS GLUCOSE MONITORING BY POTENTIAL MODULATION

(71) Applicant: Ascensia Diabetes Care Holdings AG, Basel (CH)

(72) Inventors: Huan-Ping Wu, Granger, IN (US); Mark D. Cerutti, Everett, MA (US)

(73) Assignee: Ascensia Diabetes Care Holdings AG, Basel (CH)

( * ) Notice: Subject to any disclaimer, the term of this patent is extended or adjusted under 35 U.S.C. 154(b) by 174 days.

This patent is subject to a terminal disclaimer.

(21) Appl. No.: 17/394,279

(22) Filed: Aug. 4, 2021

(65) Prior Publication Data
US 2022/0039701 A1 Feb. 10, 2022

Related U.S. Application Data

(60) Provisional application No. 63/061,135, filed on Aug. 4, 2020, provisional application No. 63/061,167, filed
(Continued)

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0002* (2013.01); *A61B 5/1451* (2013.01);
(Continued)

(58) Field of Classification Search
CPC . A61B 5/14532; A61B 5/0002; A61B 5/6801; A61B 5/725; A61B 5/1451;
(Continued)

(56) References Cited

U.S. PATENT DOCUMENTS

2005/0161346 A1 7/2005 Simpson et al.
2005/0245799 A1 11/2005 Brauker et al.
(Continued)

FOREIGN PATENT DOCUMENTS

| WO | WO2018104835 A1 | 6/2018 |
| WO | WO2020161099 A1 | 8/2020 |

OTHER PUBLICATIONS

U.S. Appl. No. 17/394,290, filed Aug. 4, 2021, Wu et al.
(Continued)

*Primary Examiner* — Jay B Shah
*Assistant Examiner* — Meghan R Kumar
(74) *Attorney, Agent, or Firm* — Erise IP, P.A.

(57) ABSTRACT

A method of determining glucose values during continuous glucose monitoring (CGM) measurements includes providing a CGM device including a sensor, a memory, and a processor; applying a constant voltage potential to the sensor; measuring a primary current signal resulting from the constant voltage potential and storing the measured primary current signal in the memory; applying a probing potential modulation sequence to the sensor; measuring probing potential modulation current signals resulting from the probing potential modulation sequence and storing measured probing potential modulation current signals in the memory; determining an initial glucose concentration based on a conversion function and a measured probing potential modulation current signal; determining a connection function value based on the primary current signal and a plurality of the probing potential modulation current signals; and determining a final glucose concentration based on the initial glucose concentration and the connection function value. Other aspects are disclosed.

20 Claims, 11 Drawing Sheets

Related U.S. Application Data on Aug. 4, 2020, provisional application No. 63/061,157, filed on Aug. 4, 2020, provisional application No. 63/061,152, filed on Aug. 4, 2020.

(51) Int. Cl.

| | | |
|---|---|---|
| *A61B 5/1486* | (2006.01) | |
| *A61B 5/1495* | (2006.01) | |
| *G01N 33/487* | (2006.01) | |
| *G01N 33/49* | (2006.01) | |
| *G16H 40/40* | (2018.01) | |
| *G16H 40/67* | (2018.01) | |
| *G16H 50/30* | (2018.01) | |
| *G16H 50/70* | (2018.01) | |

(52) U.S. Cl.
CPC .......... *A61B 5/1486* (2013.01); *A61B 5/6801* (2013.01); *A61B 5/72* (2013.01); *A61B 5/7228* (2013.01); *G01N 33/48707* (2013.01); *G01N 33/49* (2013.01); *G16H 40/67* (2018.01); *A61B 5/14865* (2013.01); *A61B 5/1495* (2013.01); *A61B 2560/0223* (2013.01); *G16H 40/40* (2018.01); *G16H 50/30* (2018.01); *G16H 50/70* (2018.01)

(58) Field of Classification Search
CPC . A61B 5/14865; A61B 5/7203; A61B 5/7275; A61B 5/6833; A61B 5/7225; A61B 5/1455; G16H 10/60; G16H 40/67; G16H 50/30
See application file for complete search history.

(56) References Cited

U.S. PATENT DOCUMENTS

| | | |
|---|---|---|
| 2010/0270178 A1 | 10/2010 | Guo et al. |
| 2013/0245401 A1* | 9/2013 | Estes .................. A61B 5/14532 600/309 |
| 2019/0346399 A1 | 11/2019 | Wu |
| 2020/0029876 A1 | 1/2020 | Brister et al. |
| 2020/0205701 A1 | 7/2020 | Bohm et al. |

OTHER PUBLICATIONS

U.S. Appl. No. 17/394,209, filed Aug. 4, 2021, Wu et al.
U.S. Appl. No. 17/394,191, filed Aug. 4, 2021, Wu.
International Search Report & Written Opinion of International Application No. PCT/EP2021/071741 dated Dec. 1, 2021.

* cited by examiner

NON-STEADY-STATE DETERMINATION OF ANALYTE CONCENTRATION FOR CONTINUOUS GLUCOSE MONITORING BY POTENTIAL MODULATION

This claims the benefit of U.S. Provisional Patent Application No. 63/061,135, filed Aug. 4, 2020 and titled "CONTINUOUS ANALYTE MONITORING SENSOR CALIBRATION AND MEASUREMENTS BY A CONNECTION FUNCTION," U.S. Provisional Patent Application No. 63/061,152, filed Aug. 4, 2020 and titled "NON-STEADY-STATE DETERMINATION OF ANALYTE CONCENTRATION FOR CONTINUOUS GLUCOSE MONITORING BY POTENTIAL MODULATION," U.S. Provisional Patent Application No. 63/061,157, filed Aug. 4, 2020 and titled "EXTRACTING PARAMETERS FOR ANALYTE CONCENTRATION DETERMINATION," and U.S. Provisional Patent Application No. 63/061,167, filed Aug. 4, 2020 and titled "BIOSENSOR WITH MEMBRANE STRUCTURE FOR STEADY-STATE AND NON-STEADY-STATE CONDITIONS FOR DETERMINING ANALYTE CONCENTRATIONS," each disclosure of which is hereby incorporated by reference herein in its entirety for all purposes.

FIELD

The present application relates generally to continuous sensor monitoring of an analyte in a bodily fluid and, more particularly, to continuous glucose monitoring (CGM).

BACKGROUND

Continuous analyte sensing in an in-vivo or in-vitro sample, such as, e.g., CGM, has become a routine sensing operation in the field of medical devices, and more specifically, in diabetes care. For biosensors that measure analytes in a whole blood sample with discrete sensing, such as, e.g., pricking a finger to obtain a blood sample, the sample's temperature and hematocrit of the blood sample may be major sources of error. However, for sensors deployed in a non-whole blood environment with relatively constant temperatures, such as sensors used in a continuous in-vivo sensing operation, other sensor error sources may exist.

Accordingly, improved apparatus and methods for determining glucose values with CGM sensors are desired.

SUMMARY

In some embodiments, a method of determining glucose values during continuous glucose monitoring (CGM) measurements includes providing a CGM device including a sensor, a memory, and a processor; applying a constant voltage potential to the sensor; measuring a primary current signal resulting from the constant voltage potential and storing the measured primary current signal in the memory; applying a probing potential modulation sequence to the sensor; measuring probing potential modulation current signals resulting from the probing potential modulation sequence and storing measured probing potential modulation current signals in the memory; determining an initial glucose concentration based on a conversion function and a measured probing potential modulation current signal; determining a connection function value based on the primary current signal and a plurality of the probing potential modulation current signals; and determining a final glucose concentration based on the initial glucose concentration and the connection function value.

In some embodiments, a continuous glucose monitoring (CGM) device includes a wearable portion having a sensor configured to produce current signals from interstitial fluid; a processor; a memory coupled to the processor; and transmitter circuitry coupled to the processor. The memory includes a connection function based on primary current signals generated by application of a constant voltage potential applied to a reference sensor, and a plurality of probing potential modulation current signals generated by application of a probing potential modulation sequence applied between primary current signal measurements. The memory includes computer program code stored therein that, when executed by the processor, causes the CGM device to measure and store a primary current signal using the sensor and memory of the wearable portion; measure and store a plurality of probing potential modulation current signals associated with the primary current signal; determine an initial glucose concentration based on a conversion function and a measured probing potential modulation current signal; determine a connection function value based on the primary current signal and a plurality of the probing potential modulation current signals; and determine a final glucose concentration based on the initial glucose concentration and the connection function value.

In some embodiments, a method of determining glucose values during continuous glucose monitoring (CGM) measurements is provided. The method includes providing a CGM device including a sensor, a memory, and a processor; applying a constant voltage potential to the sensor; measuring a primary current signal resulting from the constant voltage potential and storing the measured primary current signal in the memory; applying a probing potential modulation sequence to the sensor; measuring probing potential modulation current signals resulting from the probing potential modulation sequence and storing measured probing potential modulation current signals in the memory; determining a conversion function value based on a measured probing potential modulation current signal; determining an initial glucose concentration based on the conversion function value; determining a connection function value based on the primary current signal and a plurality of the probing potential modulation current signals; and determining a final glucose concentration based on the initial glucose concentration and the connection function value.

Still other aspects, features, and advantages of this disclosure may be readily apparent from the following detailed description and illustration of a number of example embodiments and implementations, including the best mode contemplated for carrying out the invention. This disclosure may also be capable of other and different embodiments, and its several details may be modified in various respects, all without departing from the scope of the invention. For example, although the description below is related to continuous glucose monitoring, the devices, systems, and methods described below may be readily adapted to monitoring other analytes, such as, e.g., cholesterol, lactate, uric acid, alcohol, or the like, in other continuous analyte monitoring systems.

BRIEF DESCRIPTION OF DRAWINGS

The drawings, described below, are for illustrative purposes and are not necessarily drawn to scale. Accordingly, the drawings and descriptions are to be regarded as illustrative in nature, and not as restrictive. The drawings are not intended to limit the scope of the invention in any way.

DETAILED DESCRIPTION

Embodiments described herein include systems and methods for applying probing potential modulations (PPMs) on top of the otherwise constant voltage applied to an analyte sensor. The terms "voltage," "potential," and "voltage potential" are used herein interchangeably. "Currents," "signals," and "current signals" are also used herein interchangeably, as are "continuous analyte monitoring" and "continuous analyte sensing." As used herein, PPMs refer to intentional changes made periodically to the otherwise constant voltage potential applied to a sensor during continuous analyte sensing, such as application of probing potential steps, pulses, or other potential modulations to the sensor. Use of PPMs during continuous analyte sensing may be referred to as a PP or PPM method, whereas performing continuous analyte sensing without PPMs may be referred to as a NP or NPPM method.

Figure 1A:
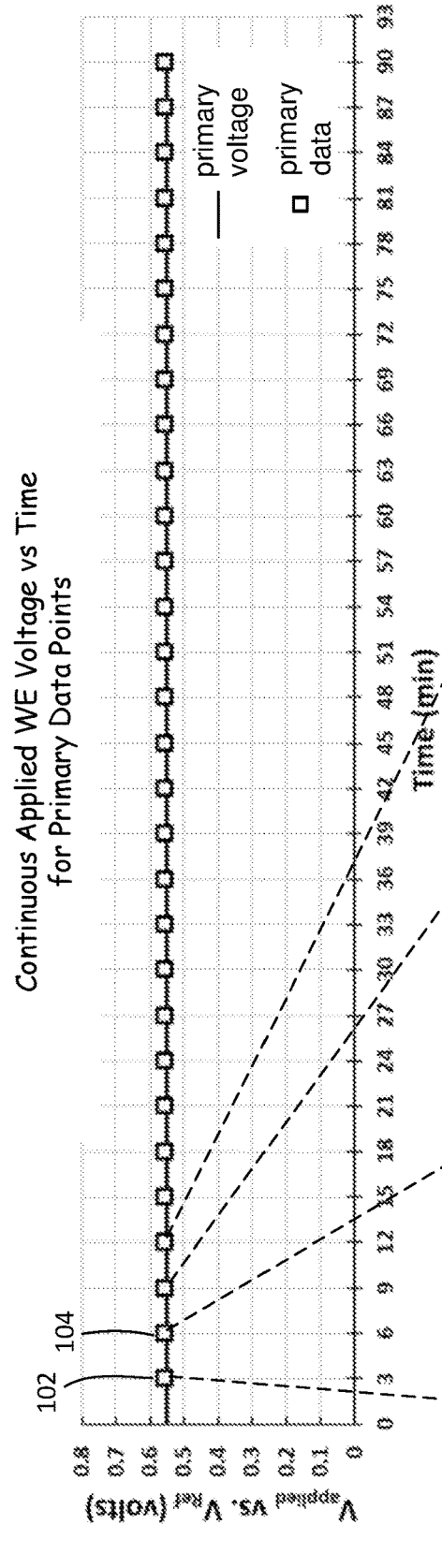
FIG. 1A illustrates a graph of applied voltage $E_0$ for a continuous glucose monitoring (CGM) sensor versus time according to one or more embodiments of the disclosure.
Figure 1B:
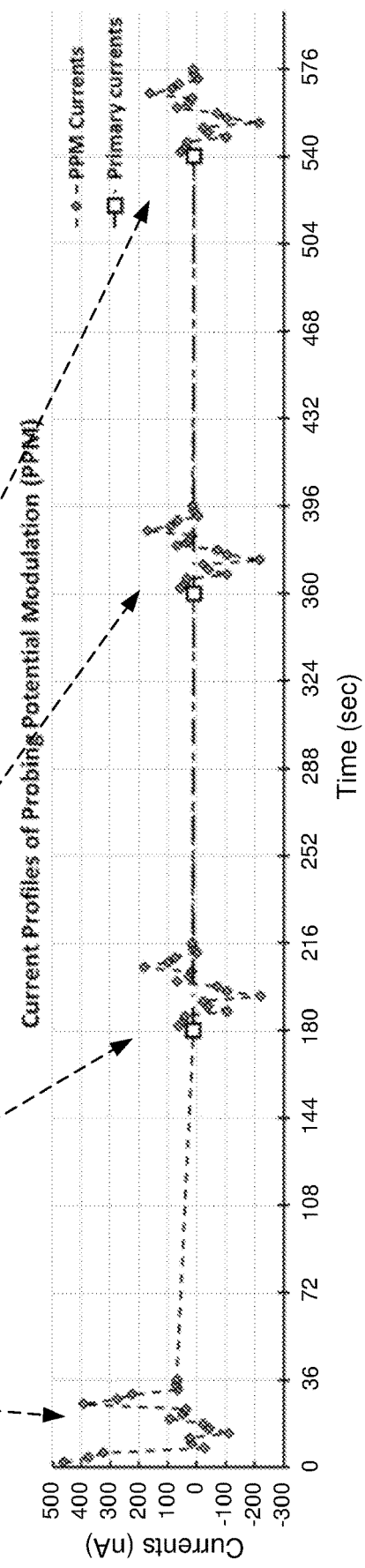
FIG. 1B illustrates a graph of current profiles of a probing potential modulation (PPM) sequence for the CGM sensor of FIG. 1A according to one or more embodiments of the disclosure.

Primary data points or primary currents refer to measurements of current signals generated in response to an analyte at a constant voltage potential applied to a sensor during continuous analyte sensing. For example, FIG. 1A illustrates a graph of applied voltage $E_0$ for a continuous glucose monitoring (CGM) sensor versus time according to one or more embodiments of the disclosure. Example times at which measurements of primary data points may be made, and subsequent PPMs may be applied, are shown. As shown in FIG. 1A, the constant voltage potential $E_0$ applied to the working electrode of an analyte sensor may be about 0.55 volts in this example. Other voltage potentials may be used. FIG. 1A shows an example of a typical cycle of the primary data points taken at a constant applied voltage. Primary data points are the data points measured or sampled at a constant applied voltage and at regular intervals, such as 3-15 minutes, during continuous glucose monitoring and are used to compute glucose values for a user. Primary data points may be working electrode currents measured for an analyte sensor during continuous analyte monitoring, for example. FIG. 1A does not show primary data points, but the time and voltage at which each primary data point is measured. For example, square 102 in FIG. 1A represents the time/voltage (3 minutes/0.55 volts) at which a first primary data point (e.g., a first working electrode current) is measured for a sensor biased at a voltage of $E_0$. Likewise, square 104 in FIG. 1A represents the time/voltage (6 minutes/0.55 volts) at which a second primary data point (e.g., second working electrode current) is measured for a sensor biased at a voltage of $E_0$.

PPM currents refer to measurements of current signals generated in response to PPMs applied to the sensor during continuous analyte sensing. PPMs are described in more detail below in connection with FIG. 2B.

Reference sensors refer to sensors used to generate primary data points and PPM currents in response to reference glucose concentrations represented by blood glucose meter (BGM) readings, for example (e.g., primary currents and PPM currents measured for the purpose of determining prediction equations such as connection functions that are subsequently stored in a continuous analyte monitoring (CAM) device and used during continuous analyte sensing to determine analyte concentrations).

Likewise, reference sensor data points refer to the reference sensor readings at times closely corresponding to the times of the signals of the sensors in continuous operation. For example, reference sensor data points may be obtained directly as the concentrations of reference analyte solutions prepared gravimetrically and verified by a reference sensor/instrument, such as a YSI glucose analyzer (from YSI Incorporated of Yellow Springs, Ohio), a Contour NEXT One (from Ascensia Diabetes Care US, Inc. of Parsippany, N.J.), and/or the like, where the in-vitro study including a linearity study is carried out by exposing the continuous analyte sensors to the reference solutions. In another example, the reference sensor data points may be obtained from the readings of a reference sensor at periodic in-vivo measurements of the target analyte through samplings of venous blood draws or finger sticks.

Unity calibration refers to a mode of calibration where only one calibration sensitivity, or one of a few subsets of calibration sensitivities, is applied to all sensors at all times. Under unity calibration, in-situ finger stick calibrations or calibration with a sensor code may be minimized or no longer needed.

For sensors deployed in a non-whole blood environment with relatively constant temperatures, such as sensors used in a continuous in-vivo sensing operation, sensor error may be related to the sensor's short and long-term sensitivity and method of calibration thereafter. There are several problems/issues associated with such a continuous sensing operation: (1) the long break-in (warmup) time, (2) the factory or in-situ calibration, and (3) the change in sensitivity during the continuous sensing operation. These issues/problems are seemingly related to the sensor sensitivity as expressed in the initial decay (break-in/warmup time), the change in sensitivity due to the susceptibility of the sensor to the environment while in sensor production, and the environments/conditions in which the sensor is thereafter deployed.

According to one or more embodiments of the disclosure, apparatus and methods are operative to probe an initial starting condition of a continuous sensor operation for a sample analyte and to probe the sensor condition at any point thereafter during the sensor's continuous sensing operation.

Methods are provided of formulating parameters for a prediction equation (e.g., connection function) that may be employed to accurately determine analyte concentrations continuously from an analyte sensor. Furthermore, a method of and apparatus for determining analyte concentrations are provided with the use of PPM self-sufficient signals (e.g., working electrode currents resulting from the application of PPMs). Such methods and apparatus may allow analyte concentration determinations while (1) overcoming the effects of different background interfering signals, (2) levelling or removing the effects of different sensor sensitivities, (3) shortening the warmup time at the beginning of a (long-term) continuous monitoring process, and/or (4) correcting sensor sensitivity changes over the continuous monitoring process. These and other embodiments are described below with reference to FIGS. 1A-8.

For a continuous glucose monitoring (CGM) biosensor, which is usually operated with a constant applied voltage, the currents from the mediator are measured continuously as a result of the enzyme oxidation of the target analyte glucose. In practice, currents are typically measured or sensed every 3 to 15 minutes or at another regular interval despite being referred to as continuous. There is an initial break-in time when the CGM sensor is first inserted/implanted into a user, which may last from 30 minutes to several hours. Once the CGM sensor is broken-in, its sensitivity may still change for various reasons. Thus, there is a need to sense the sensor's operating condition during its initial and after break-in times to identify any changes in its sensitivity.

The CGM sensor operation starts with the applied voltage $E_0$ after it is inserted/implanted subcutaneously into a user. The applied voltage $E_0$ is usually at a point on the redox plateau of the mediator. For the natural mediator of oxygen with the enzyme of glucose oxidase, the oxidation plateau of hydrogen peroxide $H_2O_2$ (the oxidation product of the enzyme reaction) ranges from about 0.5 to 0.8 volts versus an Ag/AgCl reference electrode in a media of about 100-150 mM chloride concentration. The operation potential for the glucose sensor may be set at 0.55-0.7 volts, which is within the plateau region.

Embodiments described herein employ PPMs as periodic perturbations to the otherwise constant voltage potential applied to the working electrode of a subcutaneous biosensor in a continuous sensing operation (e.g., for monitoring a biological sample analyte such as glucose). During a continuous sensing operation, such as continuous glucose monitoring, sensor working electrode current is typically sampled every 3-15 minutes (or at some other frequency) for glucose value determinations. These current measurements represent the primary currents and/or primary data points used for analyte determinations during continuous sensing operation. In some embodiments, periodic cycles of probing potential modulations may be employed after each primary current measurement so that a group of self-sufficient currents accompanies each primary data point with information about the sensor/electrode status and/or condition.

Figure 2A:
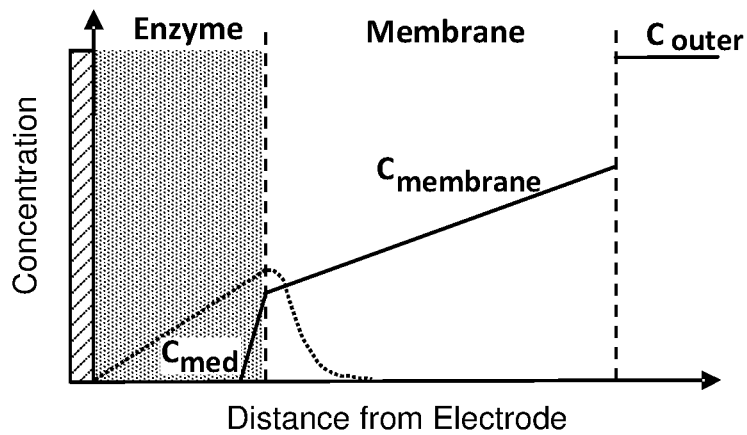
FIG. 2A illustrates a graph of a steady-state condition attended at an electrode and its nearby boundary environment according to one or more embodiments of the disclosure.
Figure 2B:
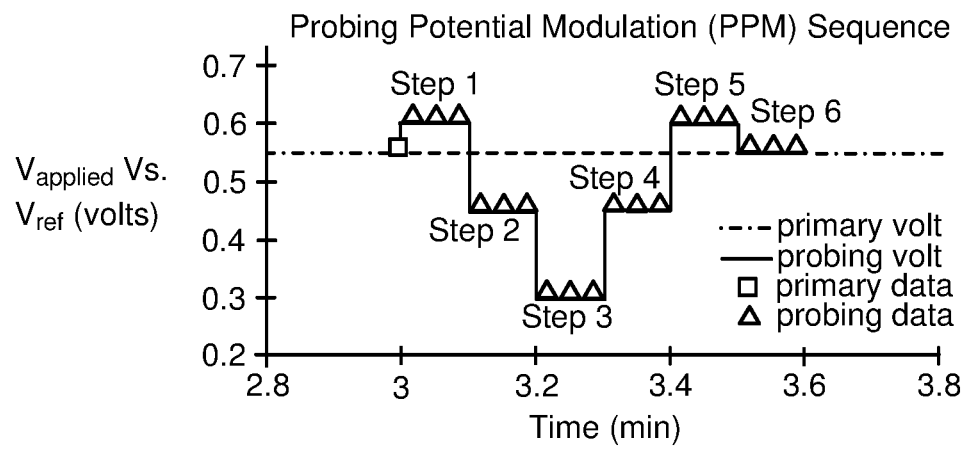
FIG. 2B illustrates a graph of an example of a probing potential modulation (PPM) sequence according to one or more embodiments of the disclosure.

PPMs may include one or more steps in potential that are different than the constant voltage potential normally used during continuous analyte monitoring. For example, PPMs may include a first potential step above or below the constant voltage potential, a first potential step above or below the constant voltage potential and then a potential step returning to the constant voltage potential, a series of potential steps above and/or below the constant voltage potential, voltage steps, voltage pulses, pulses of the same or different durations, square waves, sine waves, triangular waves, or any other potential modulations. An example of a PPM sequence is shown in FIG. 2B.

As described, conventional biosensors used in continuous analyte sensing are operated by applying a constant potential to the working electrode (WE) of the sensor. Under this condition, the currents from the WE are recorded periodically (e.g., every 3-15 minutes or at some other time interval). In this way, biosensors generate currents that are only attributable to changes in analyte concentrations, not changes in applied potential. That is, non-steady-state currents associated with the application of different potentials are avoided or minimized. While this approach simplifies the continuous sensing operation, the current signals in the data stream from application of a constant potential to the sensor provide minimum information about the sensor status/condition. That is, sensor current signals from application of a constant potential to a sensor provide little information relevant to issues associated with long-term continuous monitoring by the sensor, such as lot-to-lot sensitivity variations, the long warmup time due to initial signal decay, sensor sensitivity changes over a long-term monitoring process, effects from varying background interfering signals, or the like.

Such continuous glucose monitoring (CGM) sensors implanted subcutaneously require timely calibrations against a reference glucose value. Conventionally, the calibration process involves taking a blood glucose meter (BGM) reading from a finger stick glucose measurement, or the capillary glucose value and entering the BGM value into the CGM device to set the CGM sensor's calibration point for the next operation period. Usually, this calibration process takes place on a daily basis, or at least one finger stick glucose measurement per day as the CGM sensor's sensitivity may change from day to day. This is an inconvenient but necessary step to ensure the accuracy of the CGM sensor system.

Embodiments described herein include systems and methods for applying PPMs on top of the otherwise constant voltage applied to an analyte sensor. Methods are provided for formulating parameters for a prediction equation (e.g., a connection function) that may be employed to accurately determine analyte concentrations continuously from an analyte sensor. In some embodiments, a conversion function (e.g., based on an i43 current signal or another PPM current signal) is employed to obtain an initial glucose value, and a connection function (e.g., based on a primary current signal and PPM current signals) is then employed to obtain a final glucose value from the initial glucose value. Furthermore, methods of and systems for determining analyte concentrations with the use of probing potential modulation (PPM) self-sufficient signals are provided. Such methods and systems may allow analyte concentration determinations while (1) overcoming the effects of different background interfering signals, (2) levelling or removing the effects of different sensor sensitivities, (3) shortening the warmup time at the beginning of a (long-term) continuous monitoring process, (4) correcting sensor sensitivity changes over the continuous monitoring process, and/or (5) eliminating the need for in-situ calibrations. These and other embodiments are described below with reference to FIGS. 1A-8.

According to one or more embodiments of the disclosure, apparatus and methods are operative to use currents sampled from a non-steady-state condition during a PPM cycle for determining analyte concentrations in a continuous analyte monitoring operation. During a PPM cycle, a potential modulation is provided to the otherwise constant applied voltage of the sensor. The primary data derived from the steady-state condition and/or PPM currents derived from the non-steady-state condition may be used as an indicator of the analyte concentration, and the associated PPM currents and the PPM parameters may be used to provide information about the sensor and electrode conditions for error compensation. As will be described below, continuous monitoring sensors operated using PPM methods are in fact operated under the conditions of alternating steady-state (SS) and non-steady-state (NSS). Thus, in some embodiments, there are two concepts described herein. First, the use of currents under the non-steady-state condition, such as i43 (described below), represents a different method for determining analyte concentration in the continuous analyte monitoring operation. Second, the method of alternating between steady-state (SS) and non-steady-state (NSS) conditions for continuous analyte monitoring is another aspect of the potential modulation also disclosed for analyte concentration determination.

Steady-state condition: Conventional biosensors used in continuous analyte sensing are operated under a steady-state condition which is established when a continuous monitoring sensor is stabilized after a settling time with a constant applied potential to the working electrode (WE). Under this condition, the currents are drawn from a constant flow of incoming analyte molecules in a steady-state diffusion condition, created by the outer membrane. This condition is depicted in FIG. 2A. Under this condition, the boundary structure as defined by the enzyme layer and the outer membrane in theory creates a boundary environment to draw a constant flux of measurable species, or the reduced mediator, approximately defined by the straight line $C_{med}$. When there is no change in the analyte concentration, the current is proportional to the concentration gradient of the measurable species at the electrode surface, which is further dependent on the analyte concentration gradient as defined by the boundary condition.

The boundary environment: The boundary condition in FIG. 2A may be interpreted in theory as follows: the analyte concentration $C_{outer}$ is at some value which is in equilibrium with the membrane concentration $C_{membrane}$ at the outer interface of the membrane. The lower concentration of $C_{membrane}$ inside the membrane indicates that the membrane is designed to reduce the influx of the analyte molecules so that the biosensor operates at a steady-state condition. The relationship between $C_{outer}$ and $C_{membrane}$ is approximately governed by an equilibrium constant $K_{outer}=C_{membrane}/C_{outer}<1$. It is further governed by a lower diffusion coefficient $D_{membrane}$ than $D_{outer}$. Together the membrane permeability for the analyte $P_{membrane}=D_{membrane}*C_{membrane}$ defines the throughput of the analyte. As the analyte molecules move toward the electrode covered with enzyme, they are quickly attenuated to zero by the enzyme. Meanwhile the enzyme converts the analyte molecules into the measurable species oxidizable at the electrode, such as $H_2O_2$ with oxygen as the mediator with respect to the glucose oxidase enzyme. The measurable species will diffuse toward the electrode as well as toward the membrane once generated.

Under the constant applied voltage of fully oxidizing the measurable species, there will be a constant flux of the measurable species drawn toward the electrode. Soon, a steady-state is established where the current is proportional to the concentration gradient of the measurable species $(dC_{med}/dx)$ at the electrode surface. Under the diffusion limited condition (meaning that the oxidization/consumption rate of the measurable species is at a maximum, limited only by the diffusion of the measurable species), the concentration gradient $C_{med}$ is projected to be a straight line, defined at the electrode surface as being zero and to a point at the membrane interface which is defined by the equilibrium condition reached by multiple processes (e.g., the analyte flux entering the enzyme, the consumption and conversion of the analyte by the enzyme and the diffusion of the measurable species). The concentration $C_{med}$ into the membrane is loosely defined by diffusion. This steady-state condition changes dynamically as the outer analyte concentration changes.

In the operation condition governed by the PPM cycles, the primary data points are in fact sampled and recorded under the steady-state condition because the boundary environment resumes to the steady-state condition after each non-steady-state potential modulation cycle.

Figure 2C:
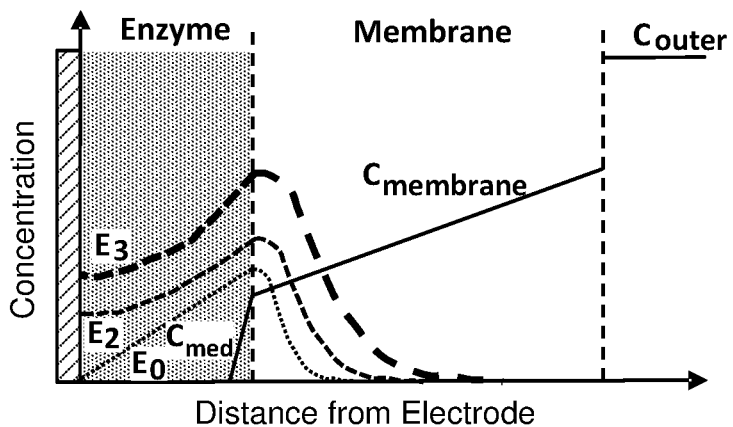
FIG. 2C illustrates a graph of a non-steady-state condition attended at an electrode and its nearby boundary environment during E2 and E3 potential steps according to one or more embodiments of the disclosure.
Figure 2D:
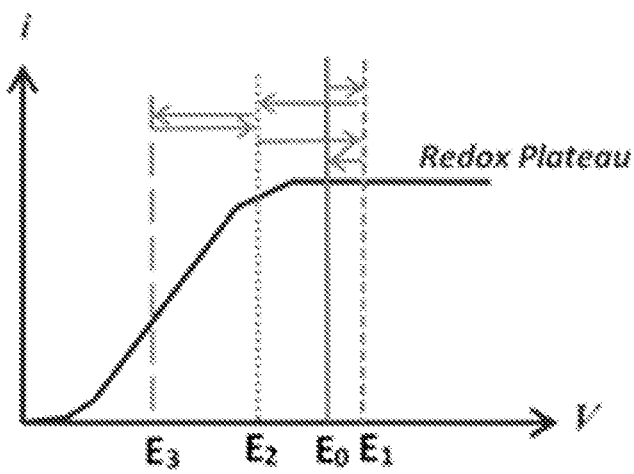
FIG. 2D illustrates a graph of an I-V curve and the individual potential steps for a PPM sequence implemented according to one or more embodiments of the disclosure.
Figure 2E:
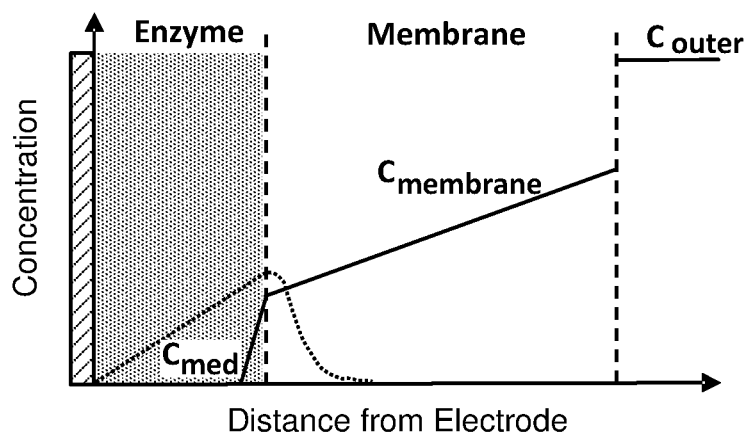
FIG. 2E illustrates a graph of a return to a steady-state (SS) condition from a non-steady-state (NSS) condition after a PPM cycle according to one or more embodiments of the disclosure.
Figure 2F:
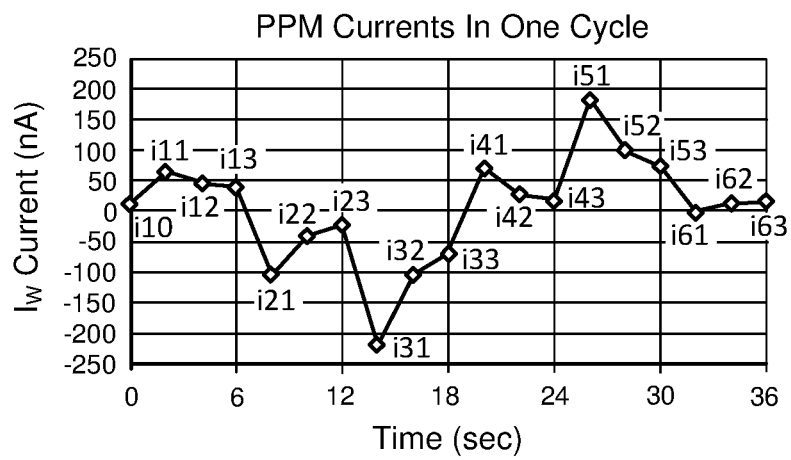
FIG. 2F illustrates a graph of typical output currents in a current implementation of the PPM sequence and the labelling of the currents in each potential step according to one or more embodiments of the disclosure.

Potential modulation and non-steady-state condition: The effects of potential modulations on non-steady-state behavior of a biosensor are described below with reference to FIGS. 2B-2F. FIG. 2B illustrates a graph of an example of a probing potential modulation (PPM) sequence according to one or more embodiments of the disclosure. In FIG. 2B, the example PPM sequence has six voltage potential steps 1-6. Other numbers, values or types of voltage potential changes may be used. FIG. 2C illustrates a graph of a non-steady-state condition attended at an electrode and its nearby boundary environment during potential steps 2 and 3 of FIG. 2B (potential steps E2 and E3 of FIG. 2D) according to one or more embodiments of the disclosure. FIG. 2D illustrates a graph of an I-V curve and the individual potential steps for a PPM sequence implemented according to one or more embodiments of the disclosure. FIG. 2E illustrates a graph of a return to a steady-state (SS) condition from a non-steady-state (NSS) condition after a PPM cycle according to one or more embodiments of the disclosure. FIG. 2F illustrates a graph of typical output currents in an example implementation of the PPM sequence and the labelling of the currents in each potential step according to one or more embodiments of the disclosure.

With reference to FIGS. 2B and 2D, if the applied potential is modulated away from the constant voltage, such as a potential step from 0.55 V to 0.6 V (step 1 in FIG. 2B and $E_0$ to $E_1$ in FIG. 2D) but still within the mediator's oxidation plateau (diffusion limited region on the V-axis), there will be some finite current generated with a small decay. This is still a faradaic process due to the asymmetrical plateau governed by $\exp(E_{app}-E^{o'})$, where $E_{app}$ is the applied voltage and $E^{o'}$ is the redox species formal potential representing its electrochemical property. This finite current with a small decay may be referred to as the plateau-degenerate current, having a slightly different oxidation state on the plateau. The current-to-voltage relationship of the mediator is approximately depicted in FIG. 2D. An example of such output current is shown and labelled as i11, i12 and i13 in FIG. 2F, while i10 is a primary current under a steady-state condition.

If the applied potential is reversed to a lower voltage, or specifically from $E_1$ to $E_2$ and further to $E_3$ in FIG. 2D (steps 2 and 3 in FIG. 2B), two things may happen: (1) the measurable species is no longer fully oxidized at the electrode surface because of the lower potential, (2) there is partial reduction of the measurable species, or the oxidized form of the mediator, with the generation of negative currents. The combined effect of these two events accumulates an excess measureable species at and near the electrode surface. Thus, the concentration profile is disrupted from the otherwise straight line condition reaching zero at the electrode surface. This condition is referred to as the non-steady-state, which is shown in FIG. 2C where $C_{med}$ is not at zero at the electrode surface. The output currents of such effect are shown as negative and labelled as i21, i22, i23 and i31, i32, i33 in FIG. 2F for steps 2 and 3 of FIG. 2B. The negative currents suggest a partial reduction of the potential steps from high to low. The disruption of the steady-state condition only occurs near the electrode surface if the process is short while the boundary environment inside and outside the membrane ($C_{membrane}$ and $C_{outer}$) remains substantially unchanged.

Alternation of NSS and SS conditions: When the potential is reversed again in step 4 of FIG. 2B (from $E_3$ to $E_2$ as shown in FIG. 2D), part of the accumulated measurable species is consumed where oxidation is at a higher rate set by the higher potential $E_2$. Even though $E_2$ is not at the plateau region of the redox species, this step provides a sudden consumption of the measurable species and produces a jump in current output from the non-steady-state concentration, and thus provides a strong indication of the concentration. Step 5 in FIG. 2B (from $E_2$ to $E_1$ in FIG. 2D) further completes the non-steady-state oxidation of the excess species to position the sensor at an operation potential on the plateau region again. Step 6 of FIG. 2B takes a negative plateau-degenerate step to return to the original potential which leads to resuming the steady-state condition before the next potential modulation cycle. Such condition is depicted in FIG. 2E, which in theory is the same as that in FIG. 2A. Thus, when the PPM cycle is repeated, the conditions of steady-state and non-steady-state are alternating, providing signals for analyte concentration determinations.

The PPM method described above provides the primary data as the indicator of the analyte concentration (although PPM currents such as i43 may provide similar information), while the associated PPM currents and the PPM parameters are the parameters providing information about the sensor and electrode condition compensation. The examples of the PPM sequences and the output current profiles all have a potential step from high to low before reversing back to high and thus the alternation of the steady-state and non-steady-state conditions.

One draw-back of operating in the steady-state condition of continuous monitoring is that other chemical species capable of passing through the membrane and being oxidizable at the electrode surface also contribute to the overall current at each sampling time. These oxidizable species are not the target analyte and thus are the interference species contributing to the overall signals. Thus, a major concern of the continuous analyte sensing is the background effect in the output currents of the sensors. Here an example is provided to illustrate this background signal effect.

Figure 3A:
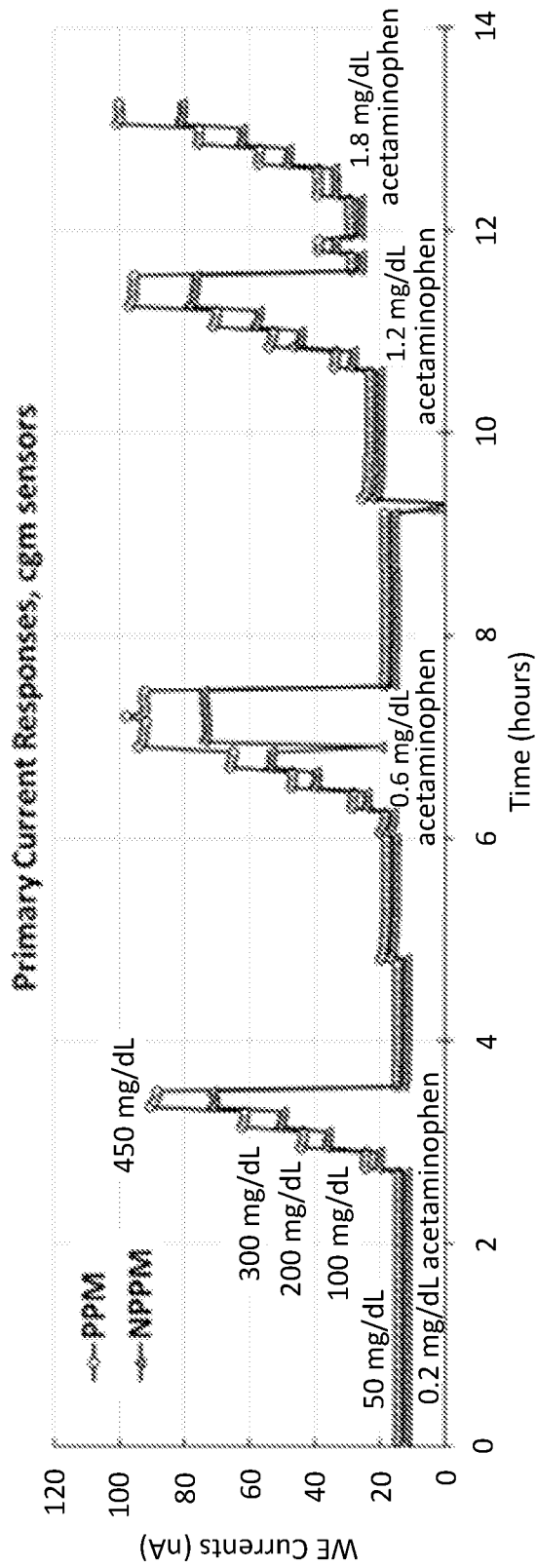
FIG. 3A illustrates a graph of temporal current profiles of the primary data points in linearity tests with four levels of acetaminophen using the PPM method and non-PPM (NPPM) method according to one or more embodiments of the disclosure.

In FIG. 3A, the currents are shown from a sensor operated with the PPM method and a sensor with the conventional operation at a constant applied voltage, in accordance with embodiments provided herein. These sensors were tested in-vitro in four sets of five glucose solutions where the glucose solutions were at four different levels of acetaminophen representing the background signals: 0.2 mg/dL, 0.6 mg/dL, 1.2 mg/dL and 1.8 mg/dL. The acetaminophen concentration of 0.2 mg/dL is considered to be equivalent to the normal level of an interfering background signal, while 0.6 mg/dL is considered to be a high level. The 1.2 and 1.8 mg/dL acetaminophen concentrations are considered to be extremely high levels. The five glucose concentrations were 50, 100, 200, 300, and 450 mg/dL for linearity study having different background acetaminophen.

Figure 3B:
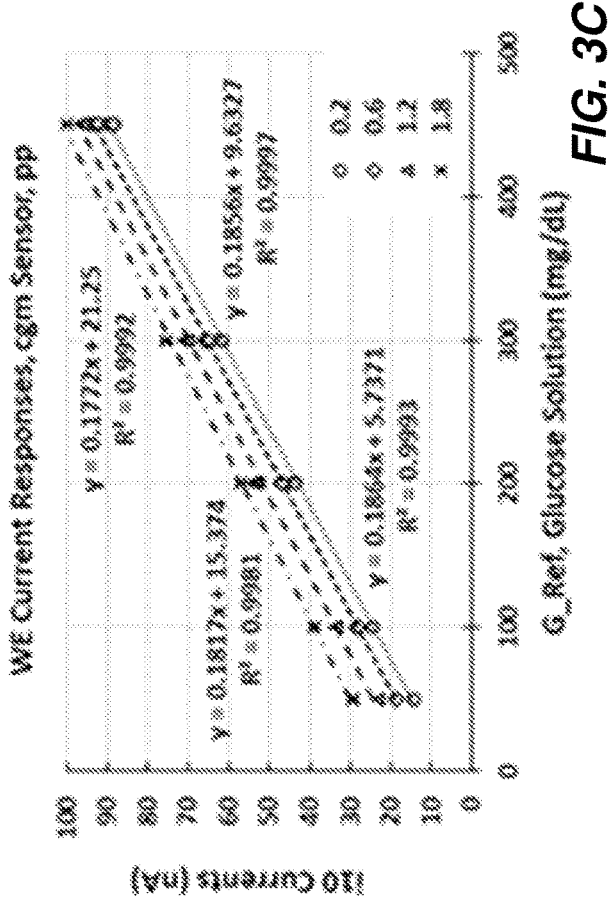
FIG. 3B illustrates a graph of primary current responses under non-PPM applied voltage to glucose in linearity tests with four levels of acetaminophen using the PPM method according to one or more embodiments of the disclosure.
Figure 3C:
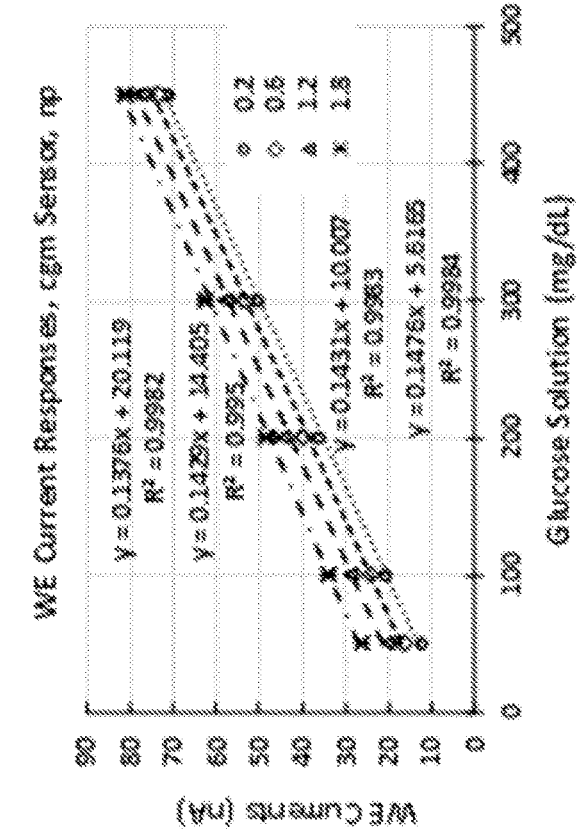
FIG. 3C illustrates a graph of primary current responses under PPM applied voltage to glucose in the same tests according to one or more embodiments of the disclosure.

The responses with respect to the glucose concentrations of the primary data points from no-PPM (NPPM or NP for brevity) and PPM (PP for brevity) biasing methods, are shown in FIGS. 3B and 3C, respectively. As shown, the effects of different background levels of acetaminophen as indicated by the intercepts are virtually the same for the NPPM and PPM methods. While the primary data points from the NPPM sensor operation, under the steady-state condition, show the dependence of the intercept on the level of the added acetaminophen, this result of the PPM primary data points having different intercept levels shows indirectly that the primary data points from the PPM methods are also from the steady-state condition, the same as the NPPM method.

Figure 3D:
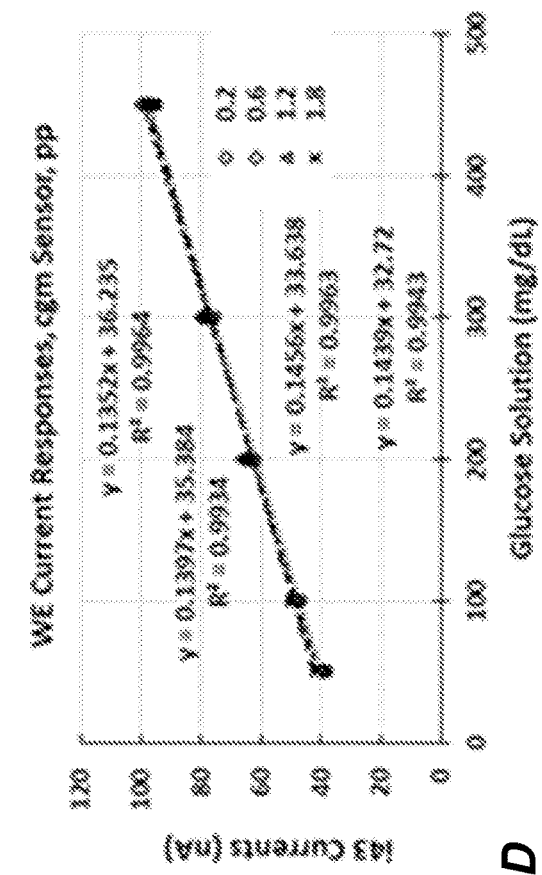
FIG. 3D illustrates a graph of the i43 current response lines under PPM applied voltage for linearity at the four levels of acetaminophen with PPM current i43 responses to glucose in the same tests according to one or more embodiments of the disclosure.

On the other hand, when a non-steady-state current, such as i43 (the last sampled current from the fourth potential modulation step as shown in FIG. 2F), is used to indicate the glucose concentration, the intercepts for four lines at four different levels of acetaminophen are virtually identical, as shown in FIG. 3D. The linearity signals by the NSS currents i43 collapse into one line from the four lines spanning in the range of 9 times the background signal concentration (ranging from 0.2 to 0.6 to 1.2 to 1.8 mg/dL acetaminophen). This result of collapsing four lines could alternatively be achieved by employing the steady-state (SS) current i10 with the PPM method and use of a predictor equation determined by regression with inputs from the PPM parameters. Furthermore, in the continuous monitoring of analyte concentration by a biosensor, the alternation of steady-state and non-steady-state conditions creates a repeated/continuous operation pattern for the analyte signals to be quantified at each NSS-SS cycle. Thus, the interference-free condition is maintained continuously, providing the basis for better signals for the analyte concentration determination.

The advantage of analyte concentration determination by the non-steady-state signals/parameters is obvious in removing the background effect on the analyte signals coming from different levels of oxidizable species in the samples. Thus, the method of non-steady-state determination of analyte concentration represents a different and unique approach to continuous analyte monitoring. The interference-free signals from the NSS condition will devote more resources (parameter terms) in regression towards further increasing the accuracy.

Figure 4A:
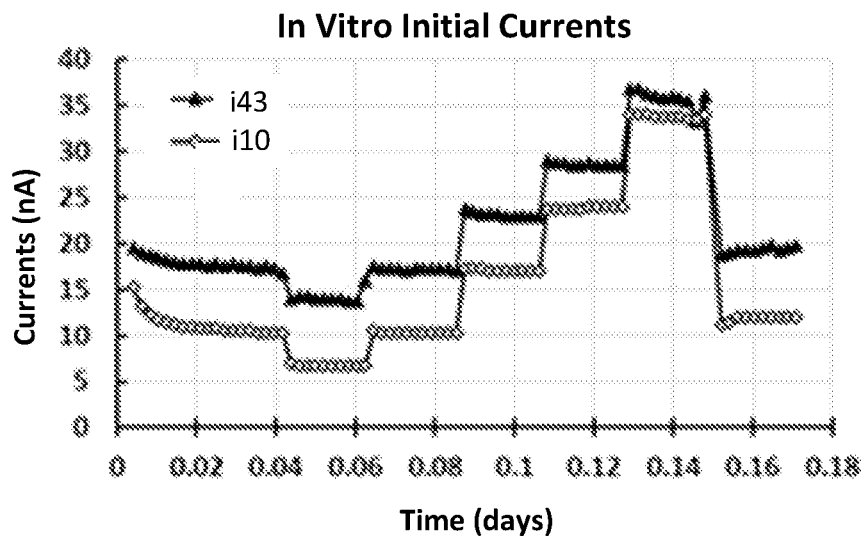
FIG. 4A illustrates a graph of initial current profiles of the SS currents i10 and NSS currents i43 in a linearity test using the PPM method according to one or more embodiments of the disclosure.
Figure 4B:
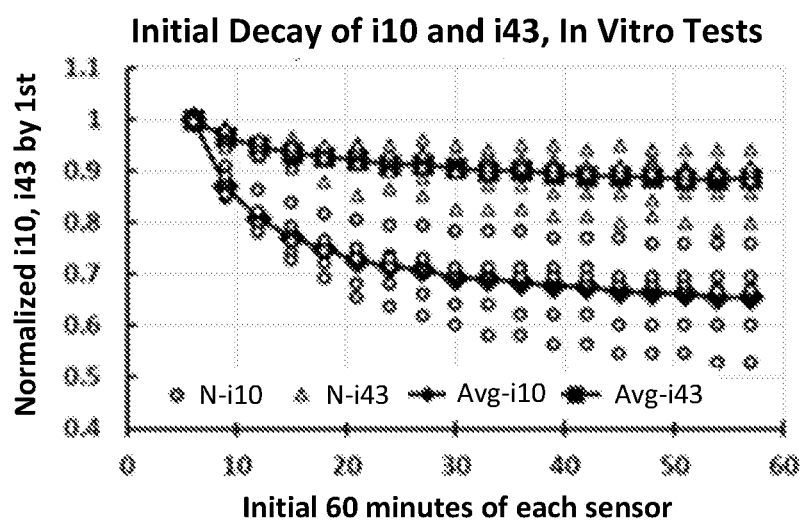
FIG. 4B illustrates a graph of individual normalized SS currents i10 and normalized NSS currents i43 as well as the average currents of these two groups in the first 60 minutes from 7 different sensors according to one or more embodiments of the disclosure.

Another advantage of NSS signals for analyte concentration determination is the substantially reduced initial decay in current of a continuous monitoring sensor, as shown in FIGS. 4A and 4B. FIG. 4A compares the steady-state current i10 and non-steady-state current i43 from a single sensor of an in-vitro linearity test. To compare the effects of the initial decay, the currents for the i10 and i43 current series in the first 60 minutes are normalized by the first current sampled. FIG. 4B shows the normalized currents from the SS (N-i10) and NSS (N-i43) currents, as well as the averages (Avg-i10, Avg-i43) of these two groups of currents from seven different CGM sensors. As shown, the initial decay of the i43 current is much smaller than that of the i10 current. That is, NSS currents are less susceptible to the initial decay than the SS currents. On average, the SS currents drop 30% in the first 30 minutes in the in-vitro tests while the NSS currents only drop 10%. This small initial decay will translate into a short warmup time for continuous monitoring sensors.

Given the uncertainty of making the one-to-one correlation between the in-vitro and in-vivo sensitivities, a method of making a connection from in-vitro to in-vivo glucose is disclosed herein by applying a unified "conversion function" to the data of a wide range of sensor responses, followed by a "connection function," or the method of unity calibration, to reduce glucose error to a narrow band. The unified conversion function computes raw or "initial" glucose values $G_{raw}$=f(signal), where signal is the measured current signal (or a parameter derived from one or more measured current signals) and f may be a linear or non-linear function. When the conversion function f is non-linear, then sensitivity or response slope is not applied (as described below).

In its simplest form, a unified conversion function may be a linear relationship between measured current signals and reference glucose levels obtained from in-vitro test data. For example, a unified conversion function may be a linear relationship between the glucose signal (e.g., Iw-Ib, i43 or another PPM current signal), a slope and reference glucose $G_{ref}$:

$$\text{Signal}=\text{slope}*G_{ref}$$

such that, $$G_{ref}=\text{signal/slope}$$

where slope represents a composite slope ($\text{slope}_{composite}$), also referred to as a unified composite slope, described below. The above relationship may then be used to calculate an initial or raw glucose $G_{raw}$ during CGM:

$$G_{raw}=\text{signal/slope}_{composite}$$

Figure 4C:
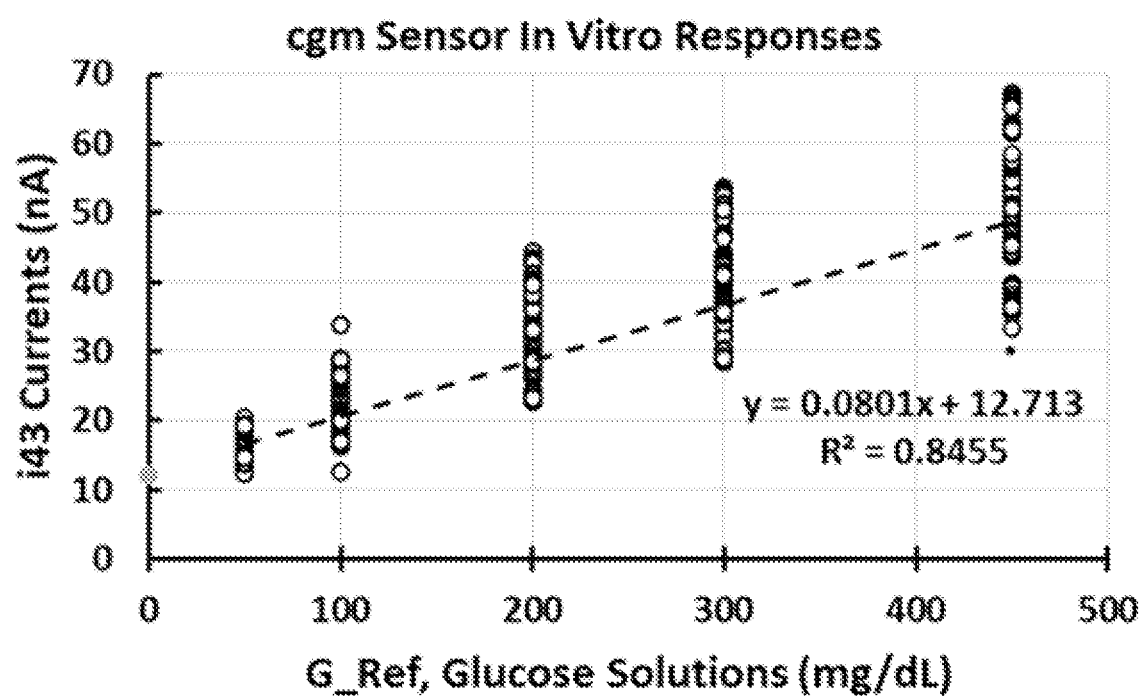
FIG. 4C illustrates i43 current versus reference glucose of in-vitro linearity tests using 10 different sensors in accordance with one or more embodiments provided herein

As described above, PPM current signals may be less sensitive to interference effects and exhibit less warmup sensitivity. For this reason, in some embodiments provided herein, the unified composite slope may be determined from PPM current signals, such as i43 or another suitable PPM current signal. For example, FIG. 4C shows the i43 current versus reference glucose of in-vitro linearity tests using 10 different sensors in accordance with embodiments provided herein. Each sensor has 3-6 linearity tests of 50, 100, 200, 300, 450 mg/dL glucose in a 15-day long term study. From this data, a conversion function may be developed using linear regression, for example. A linear regression fit to the data in FIG. 4C yields i43=0.0801*Gref+12.713. Based on this, a relationship of i43=0.0805*Gref+12 is employed, to yield a conversion function G_raw=(i43−12)/0.0805. Other relationships may be used. Note that the equivalent form of Iw−Ib for the primary data (i10) could be used. However, since the i43 is relatively indifferent about interference effects from other interference species, no background subtraction is used in this example.

In some embodiments, rather than using a linear conversion function, a non-linear conversion function, such as a polynomial, may be employed (e.g., to better fit the varied responses of sensors).

In the above example, the unified composite slope in this example is 0.0805. This composite slope is preselected from the perspective of the center of the data population as shown in FIG. 4C, but it may also be related to a subdivision of the entire response population per sensors' manufacturing specification. The unified composite slope to compute $G_{raw}$ has made the %-bias values spread out more as there is no one-to-one corresponding slope to calculate glucose for each sensor, and neither are there individual slopes for the later responses during the 15-day monitoring. However, a single conversion makes the in-vitro to in-vivo connection a simple matter without calibrations, if a connection function is applied to the individual error (% bias=100%*$\Delta$G/G=100%*($G_{raw}$−$G_{ref}$)/$G_{ref}$) to obtain the narrow band of glucose. This connection function is derived from the PPM parameters based on the $\Delta G/G_{raw}$ values. By way of such narrowing the error band from the $G_{raw}$, the connection function is referred as a connection function making connection from in-vitro to in-vivo without calibrations, meaning accommodating all responses of sensors to a narrow band of error.

A connection function is said to be a broad scope connection from the in-vitro glucose to the in-vivo glucose when the connection function provides the predicted in-vivo glucose values to a narrow band of error without calibration. In this context, it is not seeking to establish the one-to-one corresponding relationship for the in-vitro sensitivity and in-vivo sensitivity. Instead, the connection function will provide glucose values from sensors within a sensitivity range as long as the sensors are responsive to glucose. The responses may be linear, or non-linear.

Taking advantage of the rich information about CGM sensors from the PPM currents, this function is derived from the PPM currents and the associated parameters. When each response data point at the periodic cycle is converted by a composite conversion function to a glucose value $G_{raw}$, there is an error or %-bias associated with it $\Delta G/G_{raw}$=($G_{raw}$−$G_{ref}$)/$G_{ref}$. By setting $G_{connect}$=$G_{ref}$, then $G_{connect}$=$G_{raw}/(1+\Delta G/G_{raw})$=$G_{raw}$/(1+connection function)

where connection function=$\Delta G/G_{raw}$=f(PPM parameters). One way for deriving the connection function is by setting the relative error $\Delta G/G_{raw}$ as the target of the multi-variate regression and the input parameters from the PPM parameters.

Additional PPM parameters may include the normalized PPM currents ni11=i11/i10, ni12=i12/i10, . . . , ni63=i63/i10, the relative differences d11=(i11−i12)/i10, d12=(i12−i13)/i10, d21=(i21−i22)/i10, d22=(i22−i23)/i10, . . . , d61=(i61−i62)/i10, and d62=(i62−i63)/i10, the average currents of each PPM potential step av1=(i11+i12+i13)/3, av2=(i21, +i22, +i23)/3, . . . and their ratios av12=av1/av2, etc.

To summarize, in some embodiments, the i43 current may be used as part of conversion function to convert a raw current signal to a raw or initial glucose value $G_{raw}$. For example, $G_{raw}$ may be computed as:

$$G_{raw}=(i43-12.0)/0.0805$$

Other relationships between $G_{raw}$ and i43 (or other PPM current signals) may be used.

Once $G_{raw}$ is known, a connection function may then be employed to compute a compensated or final glucose signal or concentration, $G_{comp}$. For example, the connection function may be derived from in-vitro data using SS signals (i10) and NSS signals (PPM signals) as input parameters and relative error $\Delta G/G_{raw}$ as the target for multi-variate regression. An example connection function CF is provided below. It will be understood that other numbers and/or types of terms may be used.

$$\begin{aligned}CF=&24.53135+0.510036*ni53-9.90634*R53+\\&7.22965*z43-5.602442*y51+0.049372*GR1+\\&0.143765*GR3-4.875524*R61R53-\\&19.98925*R65R52-8.59255*R51R32+\\&0.348577*R54R41-0.497589*R54R42-\\&0.08465*GR61R53+0.013702*GR63R52-\\&0.0270023*GR64R41-0.115267*GR51R52+\\&0.018377*GR51R43-0.019587*GR54R43\ldots\\&-0.0339635*Gy61y65-0.123701*Gy61y52+\\&0.129388*Gy61y42+0.079116*Gy63y42+\\&0.054673*Gy63y31-0.03599*Gy65y32-\\&0.001983*Gy51y43-0.0494*Gy31y32+\\&59.1546*R61z32+18.9493*R65z53-\\&22.5024*R65z54+78.2594*R65z42+\\&7.022692*R53z41+10.90881*R53z42-\\&8.280324*R41z42+0.070284*GR65z53+\\&0.077797*GR51z42\ldots-0.022664*Gz61y52+\\&0.048962*Gz63y54+0.015388*Gz63y43-\\&0.025835*Gz64y32-0.002533*Gz51y43+\\&0.004559*Gz53y32+0.00254*Gz54y43-\\&0.000884*Gz41y43-1.17164*d61-\\&0.006599*Gd42+0.005669*Gd41+\\&6.849786*d11d31-0.939887*d21d51-\\&0.072769*d31d42+0.162176*d32d61-\\&3.714043*d42d51\ldots\end{aligned}$$

The input parameters for connection function CF may be the following types, for example.

Probing currents: The probing potential modulation currents i11, i12, i13, . . . , i61, i62, i63, wherein the first digit (x) of the ixy format denotes the potential step while the second digit (y) denotes which current measurement made after application of the potential step (e.g., the first, second or third measurement).

R parameters: These ratios are computed by the ending ppm current being divided by the first ppm current within one potential step. For example, R1=i13/i11, R2=i23/i21, R3=i33/i31, R4=i43/i41, R5=i53/i51, and R6=i63/i61.

X-type parameters: The general format for this type of parameter is given by the ending ppm current of a later potential step being divided by the ending ppm current of an earlier potential step. For example, parameter x61 is determined by i63/i13 where i63 is the ending ppm current of step 6 in the three recorded currents per step while i13 is the ending ppm current of step 1. Additionally, x61=i63/i13, x62=i63/i23, x63=i63/i33, x64=i63/i43, x65=i63/i53, x51=i53/i13, x52=i53/i23, x53=i53/i33, x54=i53/i43, x41=i43/i13, x42=i43/i23, x43=i43/i33, x31=i33/i13, x32=i33/i23, and x21=i23/i13.

Y-type parameters: The general format for this type of parameter is given by the ending ppm current of a later potential step being divided by the first ppm current of an earlier potential step. For example, parameter y61 is determined by i63/i11 where i63 is the ending ppm current of step 6 in the three recorded currents per step while i11 is the first ppm current of step 1. Additionally, y61=i63/i11, y62=i63/i21, y63=i63/i31, y64=i63/i41, y65=i63/i51, y51=i53/i11, y52=i53/i21, y53=i53/i31, y54=i53/i41, y41=i43/i11, y42=i43/i21, y43=i43/i31, y31=i33/i11, y32=i33/i21, and y21=i23/i11.

Z-type parameters: The general format for this type of parameter is given by the first ppm current of a later potential step being divided by the ending ppm current of an earlier potential step. For example, parameter z61 is determined by i61/i13 where i61 is the first ppm current of step 6 in the three recorded currents per step while i13 is the ending ppm current of step 1. Additionally, z61=i61/i13, z62=i61/i23, z63=i61/i33, z64=i61/i43, z65=i61/i53, z51=i51/i13, z52=i51/i23, z53=i51/i33, z54=i51/i43, z41=i41/i13, z42=i41/i23, z43=i41/i33, z31=i31/i13, z32=i31/i23, and z21=i21/i13.

Additional terms include normalized currents: ni11=i11/i10, ni12=i12/i10 . . . , relative differences: d11=(i11−i12)/i10, d12=(i12−i13)/i10 . . . , average currents of each PPM potential step av1=(i11+i12+i13)/3, av2=(i21+i22+i23)/3, . . . , and average current ratios av12=av1/av2, av23=av2/av3 . . . Other miscellaneous terms include GR1=$G_{raw}$*R1, Gz61=$G_{raw}$*z61, Gy52=$G_{raw}$*y52 . . . , R63R51=R63/R51, R64R43=R64/R43 . . . , z64z42=z64/z42, z65z43=z65/z43 . . . , d11d31=d11/d31, d12d32=d12/d32 . . . , Gz61y52=G*z61/y52 . . . , etc.

Other types of parameters, such as the ppm current differences or relative differences carrying the equivalent or similar information, or the ratios of middle ppm currents, may also be used.

Thus, the NSS current i43 can be used to indicate the raw glucose analyte concentration, and a connection function may be used with the raw glucose analyte concentration from i43 to connect in-vitro to in-vivo glucose. The results of compensation by the conversion function to $G_{raw}$ and the connection function to $G_{comp}$ are summarized in Table 1 which shows that both the SS signals and NSS signals are converged equivalently to a narrow error band of final analyte concentrations. The results show that i43 may be used as the analyte indicating signal and is capable of converging the wide spread responses to a narrow band of glucose values by a connection function.

TABLE 1

Summary of $G_{raw}$ and $G_{comp}$ from i10, i43 for in-vitro data set

| Indicators | | $G_{raw}$ | | $G_{comp}$ | | | |
|---|---|---|---|---|---|---|---|
| | | %-bias | %-MARD | %-bias | %-MARD | ±15% | ±20% |
| i10 (Iw-Ib) | Mean | −10.67 | 20.17 | 0.12 | 3.75 | 98.5 | 99.8 |
| | SD | 21.11 | | 5.05 | | | |
| i43 (NSS) | Mean | 3.66 | 25.25 | 2.08 | 4.11 | 97.6 | 99.2 |
| | | 33.20 | | 5.34 | | | |

In one embodiment, a connection function is provided by $G_{connect}=G_{raw}/(1+\text{connection function})$, where connection function=f(PPM parameters) derived by multivariate regression, such that the error deviated from the composite conversion function, such as the $\text{Slope}_{composite}$, is reduced/minimized to produce glucose values within a narrow band of error. In another embodiment, the connection function is simply a prediction equation by setting the $G_{Ref}$ as the regression target with multivariate regression from the PPM input parameters.

In some embodiments, the PPM cycle or sequence is designed to take no more than half of the time of the primary data cycle (e.g., 3-5 minutes) to allow sufficient time for the constant voltage applied to the working electrode for the steady-state condition to resume before the next primary data point is recorded. In some embodiments, the PPM cycle may be on the order of about 1 to 90 seconds, or no more than 50% in a regular 180-second primary data cycle.

In one or more embodiments, the PPM cycle may be about 10-40 seconds and/or include more than one modulation potential step around the mediator's redox plateau. In some embodiments, the PPM sequence may be on the order of 10-20% of the regular primary data point cycle. For instance, when the regular primary data point cycle is 180 seconds (3 minutes), a PPM cycle of 36 second is 20% of the primary data point cycle. The remaining time of the primary data cycle allows the steady-state condition to resume at the constant applied voltage. For the potential steps in the PPM cycle, the durations are of a transient nature such that the boundary conditions of the measurable species created by these potential steps are non-steady-state. Thus, each potential step may be on the order of 1-15 seconds, in some embodiments, about 3-10 seconds in other embodiments, and about 4-6 seconds in yet other embodiments.

In some embodiments, the probing potential modulation may step into the potential region of the non-diffusion-limited redox condition, or the kinetics region of the mediator (meaning the output currents are dependent on the applied voltage with the higher applied voltage producing higher output currents from the electrode). For instance, E2 and E3 of FIG. 2D (steps 2 and 3 of FIG. 2B) are two potential steps in the kinetics region of the mediator generating the non-steady-state output currents from the electrode. On reversal of the potential steps, the same magnitudes of applied voltages E2 and E1 are resumed to probe the output currents of non-steady-state from the electrode.

Different embodiments of attending non-steady-state conditions may be employed. For instance, the non-steady-state conditions may also be probed by one-step directly to the target potential E2 and returning to the starting potential E1, which is followed by a second probing potential step going directly to a different potential E3 in the kinetics region with a different non-steady-state condition, and then directly returning to the starting potential E1. The intent is to modulate the applied potentials to create the alternation of steady-state and non-steady-state conditions for the measurable species at the electrode surface whereby signals from the non-steady-state may be used for determining the analyte concentrations.

Figure 5A:
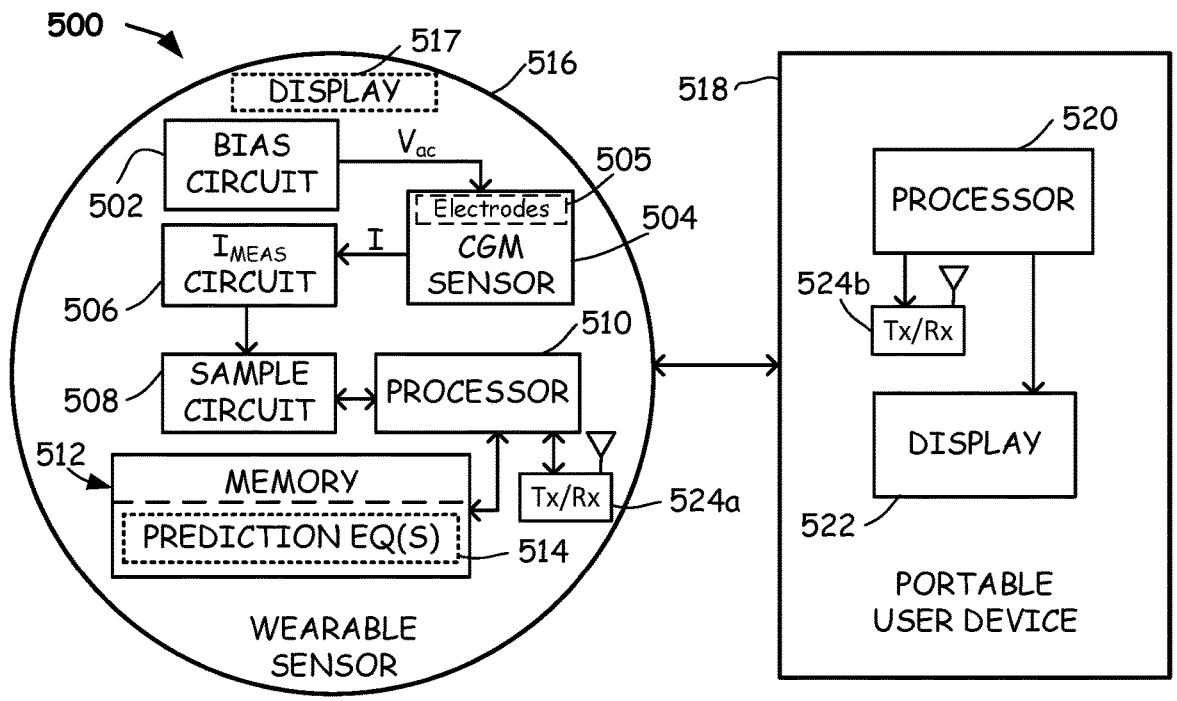
FIG. 5A illustrates a high-level block diagram of an example CGM device according to one or more embodiments of the disclosure.

FIG. 5A illustrates a high-level block diagram of an example CGM device 500 in accordance with embodiments provided herein. Although not shown in FIG. 5A, it is to be understood that the various electronic components and/or circuits are configured to couple to a power supply, such as but not limited to a battery. CGM device 500 includes a bias circuit 502 that may be configured to couple to a CGM sensor 504. Bias circuit 502 may be configured to apply a bias voltage, such as a continuous DC bias, to an analyte-containing fluid through CGM sensor 504. In this example embodiment, the analyte-containing fluid may be human interstitial fluid, and the bias voltage may be applied to one or more electrodes 505 of CGM sensor 504 (e.g., a working electrode, a background electrode, etc.).

Bias circuit 502 also may be configured to apply a PPM sequence, as shown in FIG. 2B or another PPM sequence, to CGM sensor 504. For example, PPM sequences may be applied initially and/or at intermediate time periods, or applied for each primary data point. PPM sequences may be applied before, after, or before and after measurement of a primary data point, for example.

In some embodiments, the CGM sensor 504 may include two electrodes and the bias voltage and probing potential modulations may be applied across the pair of electrodes. In such cases, current may be measured through the CGM sensor 504. In other embodiments, the CGM sensor 504 may include three electrodes such as a working electrode, a counter electrode, and a reference electrode. In such cases, the bias voltage and probing potential modulations may be applied between the working electrode and the reference electrode, and current may be measured through the working electrode, for example. The CGM sensor 504 includes chemicals which react with a glucose-containing solution in a reduction-oxidation reaction, which affects the concentration of charge carriers and the time-dependent impedance of the CGM sensor 504. Example chemicals include glucose oxidase, glucose dehydrogenase, or the like. In some embodiments, a mediator such as ferricyanide or ferrocene may be employed.

The continuous bias voltage generated and/or applied by bias circuit 502 may range from about 0.1 to 1 volts versus the reference electrode, for example. Other bias voltages may be used. Example PPM values are described previously.

PPM currents and non-PPM (NPPM) currents through CGM sensor 504 in an analyte-containing fluid responsive to PPMs and a constant bias voltage may be conveyed from CGM sensor 504 to a current measurement ($I_{meas}$) circuit 506 (also referred to as current sensing circuitry). Current measurement circuit 506 may be configured to sense and/or record current measurement signals that have magnitudes indicative of the magnitudes of the currents conveyed from CGM sensor 504 (e.g., using a suitable current-to-voltage converter (CVC), for example). In some embodiments, current measurement circuit 506 may include a resistor having a known nominal value and a known nominal precision (e.g., 0.1% to 5%, or even smaller than 0.1%, in some embodiments), through which the current conveyed from CGM sensor 504 is passed. A voltage developed across the resistor of current measurement circuit 506 represents the magnitude of the current, and may be referred to as the current measurement signal (or raw glucose signal $Signal_{Raw}$).

In some embodiments, a sample circuit 508 may be coupled to current measurement circuit 506, and may be configured to sample the current measurement signal. Sample circuit 508 may produce digitized time-domain sample data that is representative of the current measurement signal (e.g., digitized glucose signals). For example, sample circuit 508 may be any suitable A/D converter circuit configured to receive the current measurement signal, which is an analog signal, and convert it to a digital signal having a desired number of bits as an output. The number of bits output by sample circuit 508 may be sixteen in some embodiments, but more or fewer bits may be used in other embodiments. In some embodiments, sample circuit 508 may sample the current measurement signal at a sampling rate in the range of about 10 samples per second to 1000 samples per second. Faster or slower sampling rates may be used. For example, sampling rates such as about 10 kHz to 100 kHz may be used and down-sampled to further reduce signal-to-noise ratio. Any suitable sampling circuitry may be employed.

Still referring to FIG. 5A, a processor 510 may be coupled to sample circuit 508, and may be further coupled to a memory 512. In some embodiments, processor 510 and sample circuit 508 are configured to directly communicate with each other via a wired pathway (e.g., via a serial or parallel connection). In other embodiments, the coupling of processor 510 and sample circuit 508 may be by way of memory 512. In this arrangement, sample circuit 508 writes digital data to memory 512, and processor 510 reads the digital data from memory 512.

Memory 512 may have stored therein one or more prediction equations 514, such as one or more connection functions, for use in determining glucose values based on primary data points (NPPM currents) and PPM currents (from current measurement circuit 506 and/or sample circuit 508). For example, in some embodiments, two or more prediction equations may be stored in memory 512, each for use with different segments (time periods) of CGM collected data. In some embodiments, memory 512 may include a prediction equation (e.g., connection function) based on primary current signals generated by application of a constant voltage potential applied to a reference sensor and a plurality of PPM current signals generated by application of a PPM sequence applied between primary current signal measurements.

Additionally or alternatively, memory 512 may have stored there in calibration indices computed based on PPM currents for use during in-situ calibrations as described previously.

Memory 512 also may have stored therein a plurality of instructions. In various embodiments, processor 510 may be a computational resource such as but not limited to a microprocessor, a microcontroller, an embedded microcontroller, a digital signal processor (DSP), a field programmable gate array (FPGA) configured to perform as a microcontroller, or the like.

In some embodiments, the plurality of instructions stored in memory 512 may include instructions that, when executed by the processor 510, cause the processor 510 to (a) cause the CGM device 500 (via bias circuit 502, CGM sensor 504, current measurement circuit 506 and/or sample circuit 508) to measure current signals (e.g., primary current signals and PPM current signals) from interstitial fluid; (b) store current signals in memory 512; (c) compute prediction equation (e.g., conversion and/or connection function) parameters such as ratios (and/or other relationships) of currents from different pulses, voltage steps or other voltage changes within a PPM sequence; (d) employ computed prediction equation (e.g., conversion and/or connection function) parameters to compute glucose values (e.g., concentrations) using prediction equations (e.g., conversion and/or connection functions); and/or (e) communicate glucose values to a user.

Memory 512 may be any suitable type of memory, such as but not limited to, one or more of a volatile memory and/or a non-volatile memory. Volatile memory may include, but is not limited to a static random access memory (SRAM), or a dynamic random access memory (DRAM). Non-volatile memory may include, but is not limited to, an electrically programmable read-only memory (EPROM), an electrically erasable programmable read-only memory (EEPROM), a flash memory (e.g., a type of EEPROM in either of the NOR or NAND configurations, and/or in either the stacked or planar arrangements, and/or in either the single-level cell (SLC), multi-level cell (MLC), or combination SLC/MLC arrangements), a resistive memory, a filamentary memory, a metal oxide memory, a phase change memory (such as a chalcogenide memory), or a magnetic memory. Memory 512 may be packaged as a single chip or as multiple chips, for example. In some embodiments, memory 512 may be embedded, with one or more other circuits, in an integrated circuit, such as, for example, an application specific integrated circuit (ASIC).

As noted above, memory 512 may have a plurality of instructions stored therein that, when executed by processor 510, cause processor 510 to perform various actions specified by one or more of the stored plurality of instructions. Memory 512 may further have portions reserved for one or more "scratchpad" storage regions that may be used for read or write operations by processor 510 responsive to execution of one or more instructions of the plurality of instructions.

In the embodiment of FIG. 5A, bias circuit 502, CGM sensor 504, current measurement circuit 506, sample circuit 508, processor 510, and memory 512 including prediction equation(s) 514, may be disposed within a wearable sensor portion 516 of CGM device 500. In some embodiments, wearable sensor portion 516 may include a display 517 for displaying information such as glucose concentration information (e.g., without use of external equipment). Display 517 may be any suitable type of human-perceivable display, such as but not limited to, a liquid crystal display (LCD), a light-emitting diode (LED) display, or an organic light emitting diode (OLED) display.

Still referring to FIG. 5A, CGM device 500 may further include a portable user device portion 518. A processor 520 and a display 522 may be disposed within portable user device portion 518. Display 522 may be coupled to processor 520. Processor 520 may control the text or images shown by display 522. Wearable sensor portion 516, and portable user device portion 518, may be communicatively coupled.

In some embodiments, the communicative coupling of wearable sensor portion 516, and portable user device portion 518, may be by way of wireless communication via transmitter circuitry and/or receiver circuitry, such as transmit/receive circuit TxRx 524a in wearable sensor portion 516 and transmit/receive circuit TxRx 524b in portable user device 518, for example. Such wireless communication may be by any suitable means including but not limited to standards-based communications protocols such as the Bluetooth® communications protocol. In various embodiments, wireless communication between wearable sensor portion 516, and portable user device portion 518, may alternatively be by way of near-field communication (NFC), radio frequency (RF) communication, infra-red (IR) communication, or optical communication. In some embodiments, wearable sensor portion 516 and portable user device portion 518 may be connected by one or more wires.

Display 522 may be any suitable type of human-perceivable display, such as but not limited to, a liquid crystal display (LCD), a light-emitting diode (LED) display, or an organic light emitting diode (OLED) display.

Figure 5B:
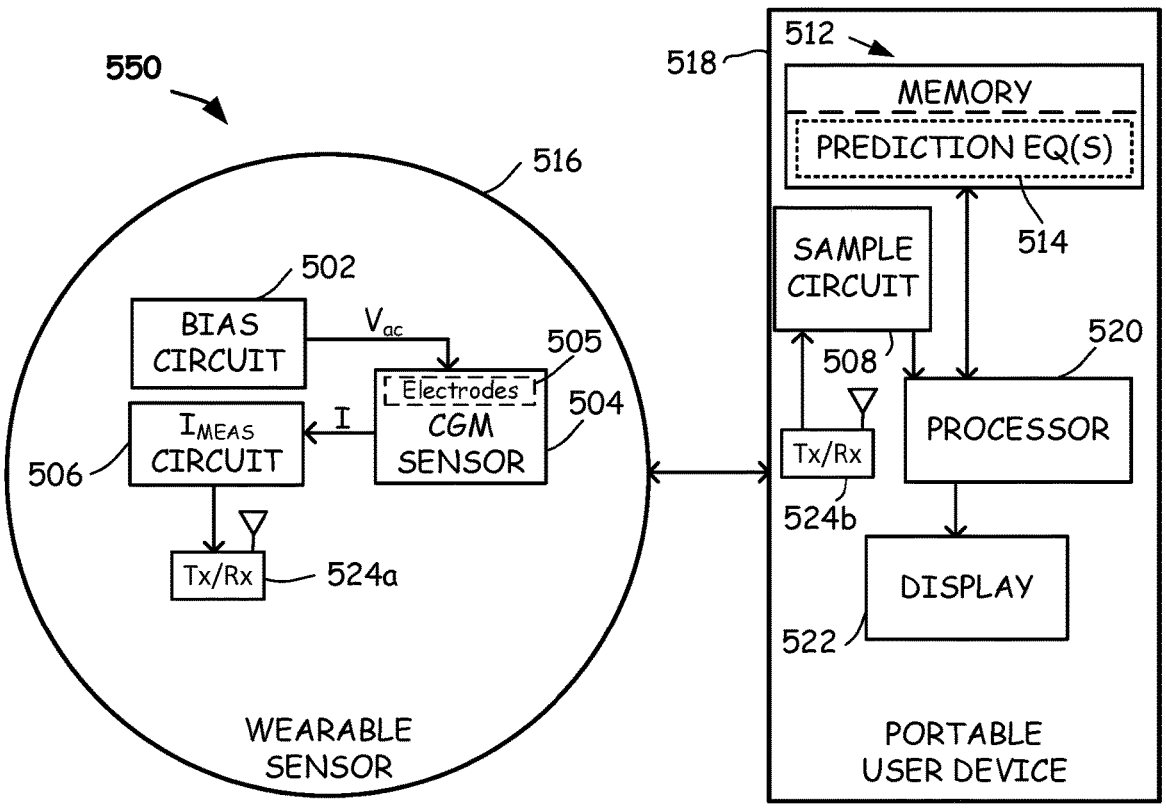
FIG. 5B illustrates a high-level block diagram of another example CGM device according to one or more embodiments of the disclosure.

Referring now to FIG. 5B, an example CGM device 550 is shown that is similar to the embodiment illustrated in FIG. 5A, but having a different partitioning of components. In CGM device 550, the wearable sensor portion 516 includes the bias circuit 502 coupled to the CGM sensor 504, and the current measurement circuit 506 coupled to the CGM sensor 504. The portable user device portion 518 of CGM device 550 includes the sample circuit 508 coupled to processor 520, and the display 522 coupled to processor 520. Processor 520 is further coupled to memory 512 that may include prediction equation(s) 514 stored therein. In some embodiments, processor 520 in CGM device 550 may also perform the previously-described functions performed by processor 510 of CGM device 500 of FIG. 5A, for example. Wearable sensor portion 516 of CGM device 550 may be smaller and lighter, and therefore less invasive, than CGM device 500 of FIG. 5A because sample circuit 508, processor 510, memory 512, etc., are not included therein. Other component configurations may be employed. For example, as a variation to the CGM device 550 of FIG. 5B, sample circuit 508 may remain on wearable sensor portion 516 (such that portable user device 518 receives digitized glucose signals from wearable sensor portion 516).

Figure 6:
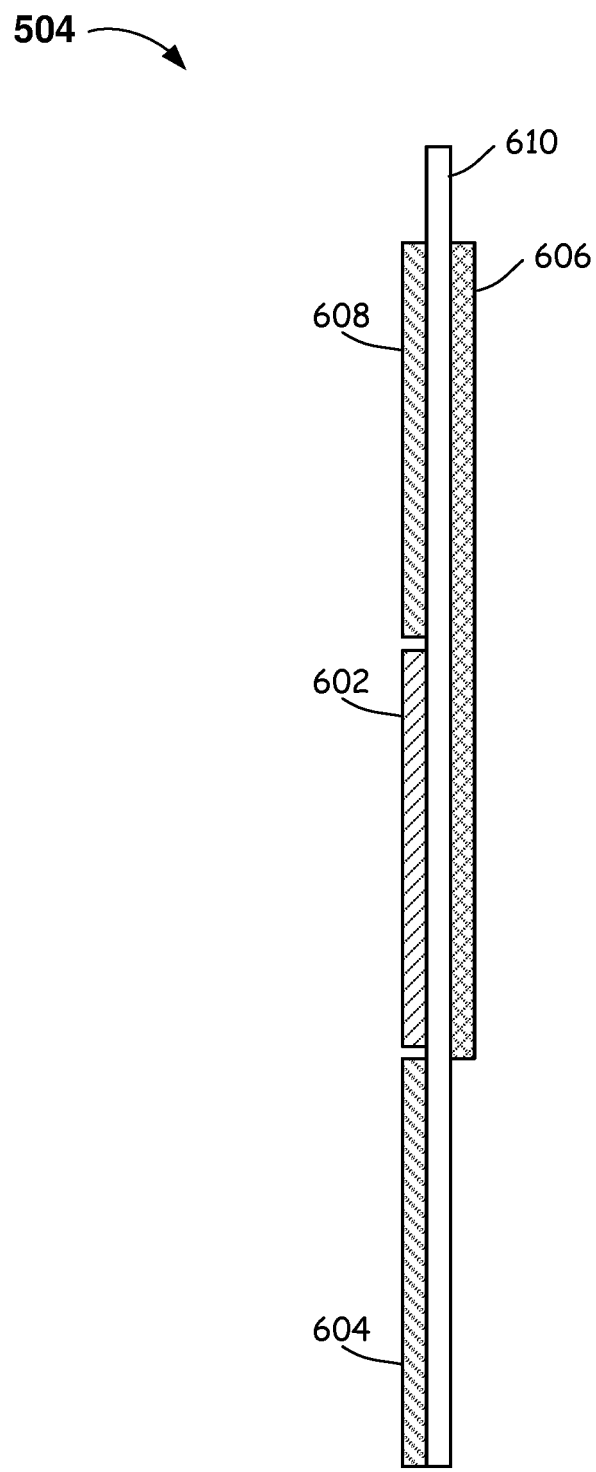
FIG. 6 is a side schematic view of an example glucose sensor according to one or more embodiments of the disclosure.

FIG. 6 is a side schematic view of an example glucose sensor 504 in accordance with embodiments provided herein. In some embodiments, glucose sensor 504 may include a working electrode 602, a reference electrode 604, a counter electrode 606 and a background electrode 608. The working electrode may include a conductive layer coated with a chemical which reacts with a glucose-containing solution in a reduction-oxidation reaction (which affects the concentration of charge carriers and the time-dependent impedance of the CGM sensor 504). In some embodiments, the working electrode may be formed from platinum or surface roughened platinum. Other working electrode materials may be used. Example chemical catalysts (e.g., enzymes) for the working electrode 602 include glucose oxidase, glucose dehydrogenase, or the like. The enzyme component may be immobilized onto the electrode surface by a cross-linking agent such as glutaraldehyde, for example. An outer membrane layer may be applied onto the enzyme layer to protect the overall inner components including the electrode and the enzyme layer. In some embodiments, a mediator such as ferricyanide or ferrocene may be employed. Other chemical catalysts and/or mediators may be employed.

In some embodiments, reference electrode 604 may be formed from Ag/AgCl. The counter electrode 606 and/or the background electrode 608 may be formed a suitable conductor such as platinum, gold, palladium, or the like. Other materials may be used for the reference, counter and/or background electrodes. In some embodiments, the background electrode 608 may be identical to the working electrode 602, but without the chemical catalyst and mediator. Counter electrode 606 may be isolated from the other electrodes by an isolation layer 610 (e.g., polyimide or another suitable material).

Figure 7:
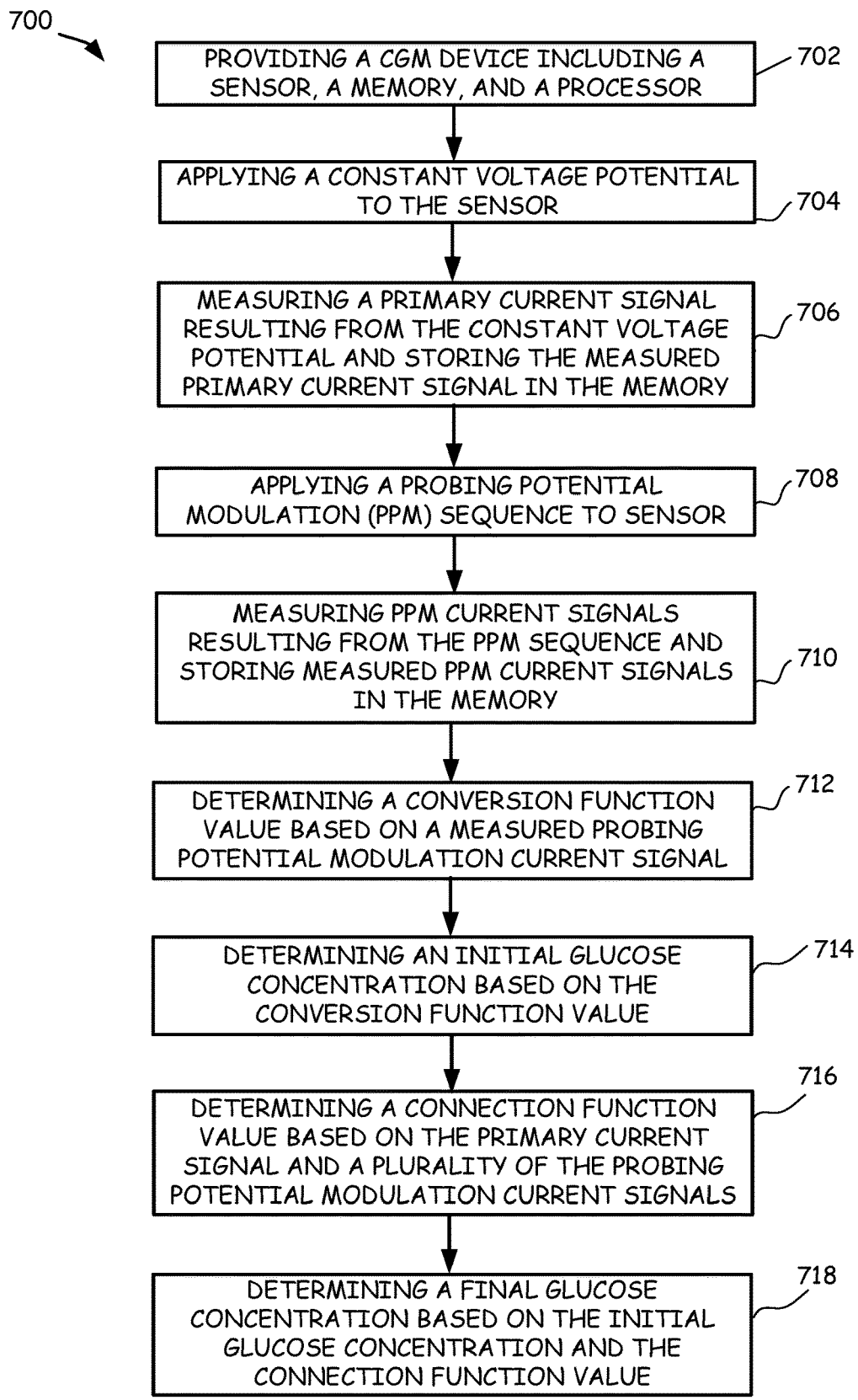
FIG. 7 illustrates an example method of determining glucose values during continuous glucose monitoring (CGM) measurements, in accordance with embodiments provided herein.

FIG. 7 illustrates an example method 700 of determining glucose values during continuous glucose monitoring (CGM) measurements, in accordance with embodiments provided herein. In some embodiments, in Block 702, method 700 includes providing a CGM device (e.g., CGM device 500) including a sensor, a memory, and a processor. In Block 704, method 700 includes applying a constant voltage potential to the sensor (e.g., about 0.55 volts or another suitable voltage). In Block 706, method 700 includes measuring a primary current signal resulting from the constant voltage potential and storing the measured primary current signal in the memory. In Block 708, method 700 includes applying a probing potential modulation sequence (e.g., as shown in FIG. 2B or another suitable PPM sequence) to the sensor. In Block 710, method 700 includes measuring probing potential modulation current signals resulting from the probing potential modulation sequence and storing measured probing potential modulation current signals in the memory. Method 700 further includes: in Block 712, determining a conversion function value based on a measured probing potential modulation current signal (e.g., i43 or another PPM current signal); in Block 714, determining an initial glucose concentration based on the conversion function value (e.g., $G_{raw}$); in Block 716, determining a connection function value based on the primary current signal and a plurality of the probing potential modulation current signals; and, in Block 718, determining a final glucose concentration (e.g., $G_{comp}$) based on the initial glucose concentration and the connection function value.

Figure 8:
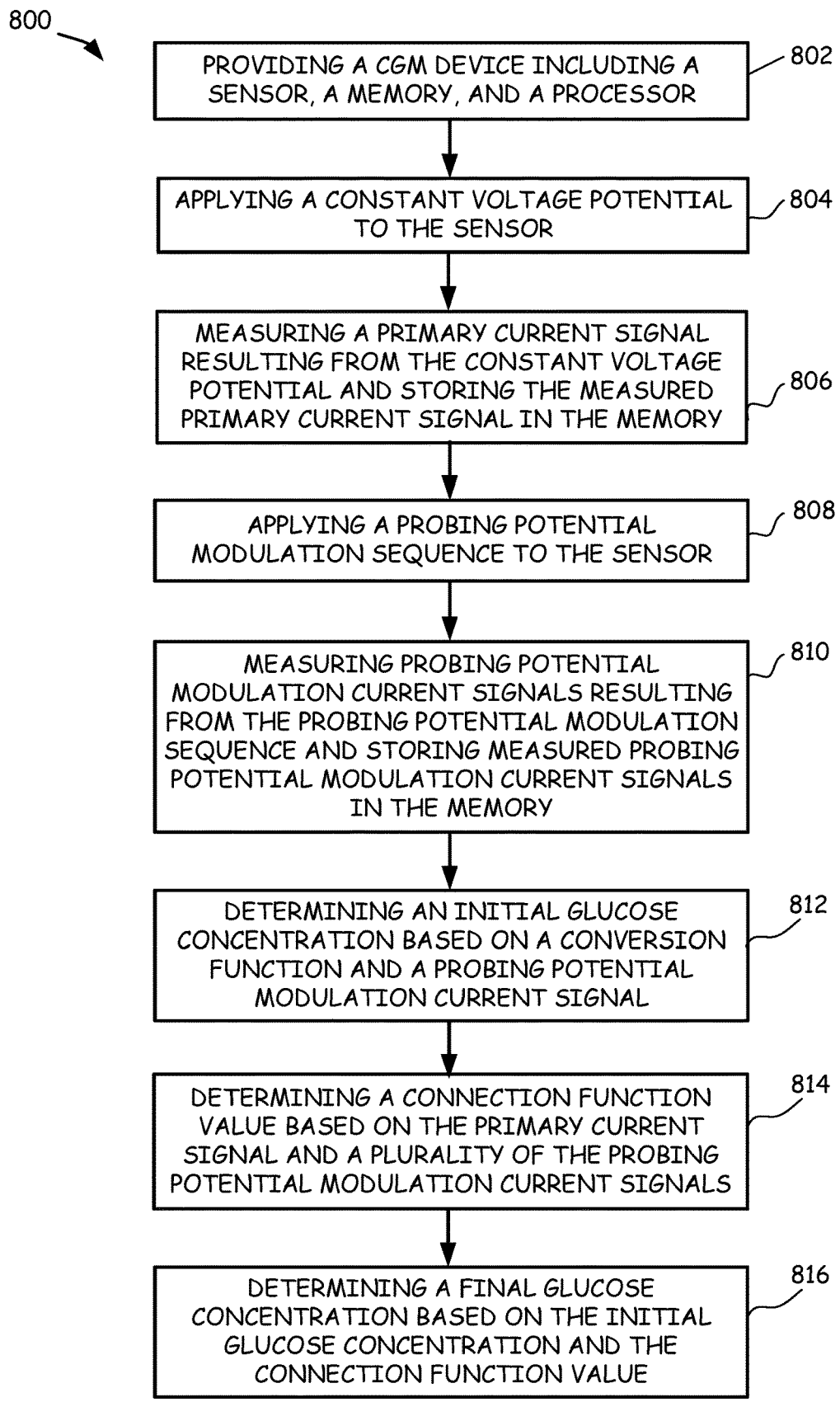
FIG. 8 illustrates another example method of determining glucose values during CGM measurements, in accordance with embodiments provided herein.

FIG. 8 illustrates another example method 800 of determining glucose values during continuous glucose monitoring (CGM) measurements, in accordance with embodiments provided herein. In some embodiments, in Block 802, method 800 includes providing a CGM device including a sensor, a memory, and a processor. In Block 804, method 800 includes applying a constant voltage potential to the sensor. In Block 806, method 800 includes measuring a primary current signal resulting from the constant voltage potential and storing the measured primary current signal in the memory. In Block 808, method 800 includes applying a probing potential modulation sequence to the sensor. In Block 810, method 800 includes measuring probing potential modulation current signals resulting from the probing potential modulation sequence and storing measured probing potential modulation current signals in the memory. In Block 812, method 800 includes determining an initial glucose concentration based on a conversion function and a measured probing potential modulation current signal. In Block 814, method 800 includes determining a connection function value based on the primary current signal and a plurality of the probing potential modulation current signals. In Block 816, method 800 includes determining a final glucose concentration based on the initial glucose concentration and the connection function value.

Note that some embodiments, or portions thereof, may be provided as a computer program product or software that may include a machine-readable medium having non-transient instructions stored thereon, which may be used to program a computer system, controller, or other electronic device to perform a process in accordance with one or more embodiments.

While the disclosure is susceptible to various modifications and alternative forms, specific method and apparatus embodiments have been shown by way of example in the drawings and are described in detail herein. It should be understood, however, that the particular methods and apparatus disclosed herein are not intended to limit the disclosure or the claims.

What is claimed is:

1. A method of determining glucose values during continuous glucose monitoring (CGM) measurements comprising:
   providing a CGM device including a sensor, a bias circuit, a memory, and a processor;
   applying a constant voltage potential to the sensor via the bias circuit;
   measuring a primary current signal resulting from the constant voltage potential and storing the measured primary current signal in the memory;
   applying a probing potential modulation sequence to the sensor,
      wherein applying the probing potential modulation sequence comprises applying a plurality of voltage potentials in sequence, each of the plurality of voltage potentials applied at a distinct time period during the continuous glucose monitoring;
   measuring a plurality of probing potential modulation current signals resulting from each of the plurality of voltage potentials in the probing potential modulation sequence and storing the plurality of measured probing potential modulation current signals in the memory,
      wherein measuring the plurality of probing potential modulation current signals comprises measuring a first output current at a start of the distinct time period for applying each one of the plurality of voltage potentials and measuring a second output current at an end of the distinct time period for applying each one of the plurality of voltage potentials such that a plurality of first output currents and a plurality of second output currents is measured for the plurality of voltage potentials in the probing potential modulation sequence,
      wherein the plurality of measured probing potential modulation current signals comprises the plurality of first output currents and the plurality of second output currents;
   determining an initial glucose concentration based on a conversion function and one of the plurality of measured probing potential modulation current signals;
   determining a connection function value based on the measured primary current signal and the plurality of measured probing potential modulation current signals,
      wherein determining the connection function value is based at least partially on a ratio of each of the plurality of second output currents relative to one of the plurality of first output currents measured at the start of the distinct time period during which each of the plurality of second output currents was measured; and
   determining a final glucose concentration based on the initial glucose concentration and the connection function value.

2. The method of claim 1,
   wherein the plurality of voltage potentials in the probing potential modulation sequence comprises a first voltage potential greater than the constant voltage potential, a second voltage potential less than the constant voltage potential, a third voltage potential less than the second voltage potential and a fourth voltage potential greater than the third voltage potential.

3. The method of claim 2,
   wherein determining the initial glucose concentration based on the conversion function and one of the plurality of measured probing potential modulation current signals comprises determining the initial glucose concentration based on the conversion function and the second output current measured during the fourth voltage potential.

4. The method of claim 2,
   wherein the second output current measured during the fourth voltage potential is a final probing potential modulation current signal measured during the fourth voltage potential.

5. The method of claim 1,
   wherein the primary current signal and probing potential modulation current signals are working electrode current signals.

6. The method of claim 1,
   wherein the primary current signal is measured every 3 to 15 minutes,
   wherein a time period between primary current signal measurements forms a primary data cycle.

7. The method of claim 6,
   wherein applying the probing potential modulation sequence occurs in half of the time period of the primary data cycle.

8. A continuous glucose monitoring (CGM) device comprising:
   a wearable portion comprising:
      a sensor configured to produce current signals from interstitial fluid;
      a processor;
      a memory coupled to the processor; and
      transmitter circuitry coupled to the processor,
      wherein the memory of the CGM device includes a connection function based on measurements of primary current signals generated by application of a constant voltage potential applied to a reference sensor, and measurements of a plurality of probing potential modulation current signals generated by application of a probing potential modulation sequence applied between primary current signal measurements,
      wherein the application of the probing potential modulation sequence comprises applying a plurality of voltage potentials in sequence, each of the plurality of voltage potentials applied at a distinct time period during a glucose monitoring period, and
      wherein the memory includes computer program code stored therein that, when executed by the processor, causes the CGM device to:
         measure and store a primary current signal using the sensor and the memory of the wearable portion;
         measure and store the plurality of probing potential modulation current signals associated with the primary current signal,
            wherein the plurality of probing potential modulation current signals comprises a first output current measured at a start of the distinct time period for applying each of the plurality of voltage potentials and a second output current measured at an end of the distinct time period for applying each of the plurality of voltage potentials such that a plurality of first output currents and a plurality of second output currents are measured for the plurality of voltage potentials;
- determine an initial glucose concentration based on a conversion function and one of the plurality of measured probing potential modulation current signals;
- determine a connection function value based on the primary current signal and the plurality of measured probing potential modulation current signals,
  - wherein the connection function value is determined based at least partially on a ratio of each of the plurality of second output currents relative to one of the plurality of first output currents measured at the start of the distinct time period during which each of the plurality of second output currents was measured; and
- determine a final glucose concentration based on the initial glucose concentration and the connection function value.

9. The CGM device of claim 8,
wherein the wearable portion is configured to apply the probing potential modulation sequence,
wherein the plurality of voltage potentials in the probing potential modulation sequence comprises a first voltage potential greater than the constant voltage potential, a second voltage potential less than the constant voltage potential, a third voltage potential less than the second voltage potential and a fourth voltage potential greater than the third voltage potential.

10. The CGM device of claim 9,
wherein the computer program code, when executed by the processor, causes the CGM device to determine the initial glucose concentration based on the second output current measured during the fourth voltage potential.

11. The CGM device of claim 10,
wherein the second output current measured during the fourth voltage potential is a final probing potential modulation current signal measured during the fourth voltage potential.

12. The CGM device of claim 8,
wherein the primary current signals and probing potential modulation current signals are working electrode current signals.

13. The CGM device of claim 8,
wherein the wearable portion further includes:
- current sensing circuitry coupled to the sensor and configured to measure current signals produced by the sensor; and
- sampling circuitry coupled to the current sensing circuitry and configured to generate digitized current signals from the measured current signals.

14. The CGM device of claim 8 further comprising:
a portable user device, the portable user device including receiver circuitry and a display, and wherein the transmitter circuitry of the wearable portion is configured to communicate glucose values to the receiver circuitry of the portable user device for presentation to a user of the CGM device.

15. A method of determining glucose values during continuous glucose monitoring (CGM) comprising:
- providing a CGM device including a sensor, a memory, and a processor;
- applying a constant voltage potential to the sensor during the continuous glucose monitoring,
  - wherein the continuous glucose monitoring comprises a plurality of distinct time periods;
- measuring a primary current signal resulting from the constant voltage potential and storing the primary current signal in the memory;
- applying a probing potential modulation sequence to the sensor,
  - wherein applying the probing potential modulation sequence further comprises:
    - applying a first voltage potential at a first distinct time period, and
    - applying a second voltage potential at a second distinct time period immediately subsequent to the first distinct time period;
- measuring probing potential modulation current signals resulting from the probing potential modulation sequence and storing measured probing potential modulation current signals in the memory,
  - wherein measuring the probing potential modulation current signals further comprises:
    - measuring a first probing current during the first distinct time period for applying the first voltage potential, and
    - measuring a second probing current during the second distinct time period for applying the second voltage potential;
- determining a conversion function value based on one of the measured probing potential modulation current signals;
- determining an initial glucose concentration based on the conversion function value;
- determining a connection function value based on the primary current signal and the measured probing potential modulation current signals,
  - wherein the connection function value is determined based at least partially on a ratio of the second probing current relative to the first probing current; and
- determining a final glucose concentration based on the initial glucose concentration and the connection function value.

16. The method of claim 15,
wherein the first voltage potential is greater than the constant voltage potential and the second voltage potential is less than the constant voltage potential,
wherein applying the probing potential modulation sequence further comprises applying a third voltage potential less than the second voltage potential and a fourth voltage potential greater than the third voltage potential.

17. The method of claim 16,
wherein determining the conversion function value based on one of the measured probing potential modulation current signals comprises determining the conversion function value based on a fourth probing current measured during the fourth voltage potential.

18. The method of claim 17,
wherein the fourth probing current measured during the fourth voltage potential is a final probing potential modulation current signal measured during the fourth voltage potential.

19. The method of claim 15,
wherein the primary current signal is measured every 3 to 15 minutes,
wherein a time period between primary current signal measurements forms a primary data cycle.

20. The method of claim 19,
wherein applying the probing potential modulation sequence occurs in half of the time period of the primary data cycle.

* * * * *